(12) United States Patent
Rush et al.

(10) Patent No.: US 12,708,412 B2
(45) Date of Patent: Aug. 18, 2026

(54) BONE FRACTURE FIXATION DEVICE AND RELATED SYSTEMS AND METHODS

(71) Applicant: Surgical Design Innovations II, LLC, Johnston, IA (US)

(72) Inventors: Shannon M. Rush, San Jose, CA (US); Troy J. Boffeli, Woodbury, MN (US); Graham Hamilton, Concord, CA (US); Michael Lee, Johnston, IA (US); Jordan Grossman, Akron, OH (US); Mark Hardy, Lakewood, OH (US); Brogan McGuire, Johnston, IA (US)

(73) Assignee: Surgical Design Innovations II, LLC, Johnston, IA (US)

( * ) Notice: Subject to any disclaimer, the term of this patent is extended or adjusted under 35 U.S.C. 154(b) by 163 days.

(21) Appl. No.: 18/399,834

(22) Filed: Dec. 29, 2023

(65) Prior Publication Data

US 2024/0130764 A1 Apr. 25, 2024

Related U.S. Application Data

(63) Continuation-in-part of application No. 17/859,529, filed on Jul. 7, 2022, now Pat. No. 12,042,190.

(60) Provisional application No. 63/499,619, filed on May 2, 2023, provisional application No. 63/477,737, filed on Dec. 29, 2022, provisional application No. 63/219,112, filed on Jul. 7, 2021.

(51) Int. Cl.
*A61B 17/72* (2006.01)
*A61B 17/16* (2006.01)
*A61B 17/00* (2006.01)

(52) U.S. Cl.
CPC ...... *A61B 17/7291* (2013.01); *A61B 17/1624* (2013.01); *A61B 2017/00477* (2013.01)

(58) Field of Classification Search
CPC ........................................... A61B 17/72–7291
See application file for complete search history.

(56) References Cited

U.S. PATENT DOCUMENTS 5,116,378 A * 5/1992 Carbone ............ A61B 17/7258 623/23.26
5,993,448 A 11/1999 Remmler
7,703,727 B2 * 4/2010 Selness ................ A47B 91/028 248/188.2
8,562,683 B2 10/2013 Mckinley
(Continued)

FOREIGN PATENT DOCUMENTS

WO 2019155160 A1 8/2019

OTHER PUBLICATIONS

International Searching Authority "International Search Report and Written Opinion" From Application No. PCT/US2023/086338, Mailed Apr. 19, 2024, pp. 1-10.

*Primary Examiner* — Eduardo C Robert
*Assistant Examiner* — Steven J Cotroneo
(74) *Attorney, Agent, or Firm* — Fredrikson & Byron, P.A.

(57) ABSTRACT

The various embodiments disclosed herein relate to bone fixation devices, including intramedullary fixation or fusion devices. The various devices disclosed include an intermedullary device having a proximal member and a distal member that is articulable in relation to the proximal member. The proximal and distal members have ends that are movably coupled to form a joint that can be actuated to reduce a fracture and realign the bone after insertion of the device into the bone.

20 Claims, 19 Drawing Sheets

(56) References Cited

U.S. PATENT DOCUMENTS 10,492,839 B2 * 12/2019 Wodajo .............. A61B 17/7225
10,751,094 B2 * 8/2020 Green ................ A61B 17/7053
2008/0269751 A1 * 10/2008 Matityahu .......... A61B 17/7283 606/301
2009/0216232 A1 * 8/2009 Buford, III ........ A61B 17/8869 29/244
2011/0066152 A1 * 3/2011 Keller .................. A61B 17/725 606/62
2011/0282395 A1 * 11/2011 Beyar ................ A61B 17/7233 606/301
2012/0065638 A1 * 3/2012 Moore ............... A61B 17/7225 606/62
2013/0150971 A1 * 6/2013 DeFalco ................... A61F 2/44 623/17.16
2013/0325006 A1 * 12/2013 Michelinie ......... A61B 17/1725 606/62
2013/0325007 A1 * 12/2013 Beyar .................. A61B 17/725 606/62
2013/0325076 A1 * 12/2013 Palmer ............... A61B 17/8635 606/104
2019/0015138 A1 * 1/2019 Schwardt ........... A61B 17/7216

* cited by examiner 50
54
82
80
58
52
70
90
88
56

50
54
80
74
60A
58
60B
62
62A
60
70
62B
52
76
77
86
72
84
92
56
96
94

150
152
154
154A
154b
156
158
160A
160B
160C
162A
162B
162C
164A
164B
166A
166B 150
154
154A
154B
156
158
160A
160B
160C
162A
162B
162C
164A
164B
166A
166B

BONE FRACTURE FIXATION DEVICE AND RELATED SYSTEMS AND METHODS

CROSS-REFERENCE TO RELATED APPLICATION(S)

This application claims the benefit under 35 U.S.C. § 119(e) to U.S. Provisional Application 63/477,737, filed Dec. 29, 2022 and entitled "Bone Fracture Fixation Device and Related Systems and Methods," and to U.S. Provisional Application 63/499,619, filed May 2, 2023 and entitled "Bone Fracture Fixation Device and Related Systems and Methods." In addition, this application also claims priority as a continuation-in-part to U.S. patent application Ser. No. 17/859,529, filed Jul. 7, 2022 and entitled "Bone Fracture Fixation Device and Related Systems and Methods," which claims the benefit under 35 U.S.C. § 119(e) to U.S. Provisional Application 63/219,112, filed Jul. 7, 2021 and entitled "Bone Fracture Fixation Device and Related Systems and Methods." All of the above applications are hereby incorporated herein by reference in their entireties.

FIELD

The various embodiments disclosed herein relate to bone fixation or fusion devices, including intramedullary fixation or fusion devices that are implanted into a target bone. In addition, other embodiments relate to systems and methods for implantation and adjustment of the bone fixation or fusion devices.

BACKGROUND

Bone fractures and dislocations, including fibular fractures and syndesmosis dislocations, are common injuries that currently require correction via known fracture/dislocation fixation devices and procedures. The known fracture and/or dislocation fixation devices and systems typically include a central nail and locking screws. Once the nail is implanted within the intramedullary canal of the target bone, there is little or no ability to adjust the nail or reduce the fracture. This lack of adjustability can result in poor reduction of the fracture, which can lead to poor or delayed healing and/or ankle misalignment.

There is a need in the art for improved intramedullary devices and systems for treatment of bone fractures and dislocations, including fibular fractures and syndesmosis dislocations.

BRIEF SUMMARY

Discussed herein are various bone fixation or fusion devices and related systems and methods.

In Example 1, a bone fixation device comprises a device body comprising a proximal member, a distal member, and a drive mechanism operably coupled to the proximal and distal members. The proximal member comprises a proximal lumen defined within the proximal member, wherein the proximal lumen is parallel to a longitudinal axis of the proximal member, a drive slot defined within the proximal member and in fluidic communication with the proximal lumen, wherein the drive slot is transverse to the longitudinal axis of the proximal member, and a distal end having a distal face disposed at a angle ranging from 1 degree to 89 degrees in relation to the longitudinal axis of the proximal. The distal member comprises a proximal end having a proximal face disposed at an angle corresponding to the angle of the distal face such that the proximal end is in slidable contact with the distal end, wherein the proximal member and the distal member are slidable radially and axially in relation to each other via the distal end of the proximal member and the proximal end of the distal member, and a distal lumen defined within the distal member, wherein the distal lumen is parallel to a longitudinal axis of the distal member, wherein the distal lumen is in fluidic communication with the proximal lumen. The drive mechanism comprises a linear drive shaft slidably disposed within the proximal lumen and the distal lumen and a rotatable drive structure rotatably disposed within the distal lumen. The linear drive shaft comprises a first engagement structure disposed at a distal end of the linear drive shaft and at least one proximal member engagement structure disposed at a proximal end of the linear drive shaft, wherein the at least one proximal member engagement structure is slidably disposed within the drive slot. The rotatable drive structure comprises a second engagement structure disposed at a proximal end of the rotatable drive structure, wherein the second engagement structure is operably coupled with the first engagement structure.

Example 2 relates to the device according to Example 1, further comprising at least one fixation lumen defined through the distal member, wherein the at least one fixation lumen is transverse to the longitudinal axis of the distal member, wherein the at least one fixation lumen is in fluidic communication with the distal lumen.

Example 3 relates to the device according to Example 2, further comprising at least one transverse lumen defined through the linear drive shaft, wherein the at least one transverse lumen is transverse to a longitudinal axis of the linear drive shaft, wherein the at least one transverse lumen is in fluidic communication with the at least one fixation lumen.

Example 4 relates to the device according to Example 1, wherein rotation of the rotatable drive structure within the distal lumen causes the linear drive shaft to move axially within the distal lumen and the proximal lumen.

Example 5 relates to the device according to Example 1, wherein the rotatable drive structure is threadably coupled to an inner surface of the distal lumen.

Example 6 relates to the device according to Example 1, wherein the linear drive shaft comprises a proximal section comprising a proximal section diameter and a distal section comprising a distal section diameter, wherein the distal section diameter is greater than the proximal section diameter.

Example 7 relates to the device according to Example 1, wherein the at least one fixation lumen comprises threads defined in an inner wall of the at least one fixation lumen.

In Example 8, a bone fixation device comprises a device body comprising a proximal member and a distal member, an adjustable joint formed between the proximal member and the distal member, and a drive mechanism operably coupled to the proximal and distal members. The proximal member comprises a shaft lumen defined within the proximal member, wherein the shaft lumen is parallel to a longitudinal axis of the proximal member and a drive slot defined with the proximal member, wherein the drive slot is transverse to the longitudinal axis of the proximal member. The distal member comprises a drive mechanism lumen defined within the distal member, wherein the drive mechanism lumen is parallel to a longitudinal axis of the distal member and at least one fixation lumen defined within the distal member, wherein the at least one fixation lumen is transverse to the longitudinal axis of the distal member, wherein the at least one fixation lumen is in fluidic communication with the drive mechanism lumen. With respect to the adjustable joint, the proximal member and the distal member are movable radially and axially in relation to each other via the adjustable joint. The drive mechanism comprises a rotatable drive structure rotatably disposed within the drive mechanism lumen, wherein the rotatable drive structure comprises a rotatable engagement structure disposed at a proximal end of the rotatable drive structure and a linear drive shaft slidably disposed within the drive mechanism lumen. The linear drive shaft comprises a stationary engagement structure disposed at a distal end of the linear drive shaft, wherein the stationary engagement structure is configured to couple with the rotatable engagement structure, at least one transverse lumen defined through the linear drive shaft, wherein the at least one transverse lumen is transverse to a longitudinal axis of the linear drive shaft, wherein the at least one transverse lumen is in fluidic communication with the at least one fixation lumen, and at least one protrusion disposed at a proximal end of the linear drive shaft, wherein the at least one protrusion is slidably disposed within the drive slot.

Example 9 relates to the device according to Example 8, wherein rotation of the rotatable drive structure within the drive mechanism lumen causes the linear drive shaft to move axially within the drive mechanism lumen.

Example 10 relates to the device according to Example 8, wherein the rotatable drive structure is threadably coupled to an inner surface of the drive mechanism lumen.

Example 11 relates to the device according to Example 8, wherein the at least one fixation lumen comprises first and second fixation lumens, wherein the first fixation lumen has a longitudinal axis that is transverse to a longitudinal axis of the second fixation lumen.

Example 12 relates to the device according to Example 11, wherein the at least one transverse lumen comprises first and second transverse lumens, wherein the first transverse lumen has a longitudinal axis that is transverse to a longitudinal axis of the second transverse lumen.

Example 13 relates to the device according to Example 8, wherein the linear drive shaft comprises a proximal section comprising a proximal section diameter and a distal section comprising a distal section diameter, wherein the distal section diameter is greater than the proximal section diameter.

Example 14 relates to the device according to Example 13, wherein the at least one transverse lumen is defined in the distal section.

Example 15 relates to the device according to Example 8, further comprising a removable cap, wherein the removable cap is removably coupleable to a distal opening defined in the distal member, wherein the distal opening is in fluidic communication with the drive mechanism lumen.

Example 16 relates to the device according to Example 8, wherein the at least one fixation lumen comprises threads defined in an inner wall of the at least one fixation lumen.

In Example 17, a bone fixation device comprises a device body comprising a proximal member and a distal member, a slidable joint formed between the proximal member and the distal member, wherein the distal member is movable radially and axially in relation to the proximal member via the slidable joint, and a drive mechanism operably coupled to the proximal and distal members. The proximal member comprises a proximal lumen defined within the proximal member, wherein the proximal lumen is parallel to a longitudinal axis of the proximal member, and a drive slot defined with the proximal member and in fluidic communication with the proximal lumen, wherein the drive slot is transverse to the longitudinal axis of the proximal member. The distal member comprises a distal lumen defined within the distal member, wherein the distal lumen is parallel to a longitudinal axis of the distal member, wherein the distal lumen is in fluidic communication with the proximal lumen, and at least one fixation lumen defined within the distal member, wherein the at least one fixation lumen is transverse to the longitudinal axis of the distal member, wherein the at least one fixation lumen is in fluidic communication with the distal lumen. The drive mechanism comprises a rotatable drive structure rotatably disposed within the distal lumen, wherein the rotatable drive structure comprises a first engagement structure disposed at a proximal end of the rotatable drive structure and a linear drive shaft slidably disposed within the proximal lumen and the distal lumen. The linear drive shaft comprises a second engagement structure disposed at a distal end of the linear drive shaft, wherein the second engagement structure is operably coupled with the first engagement structure, at least one transverse lumen defined through the linear drive shaft, wherein the at least one transverse lumen is transverse to a longitudinal axis of the linear drive shaft, wherein the at least one transverse lumen is in fluidic communication with the at least one fixation lumen, and at least one radial protrusion disposed at a proximal end of the linear drive shaft, wherein the at least one radial protrusion is slidably disposed within the drive slot.

Example 18 relates to the device according to Example 17, wherein the first engagement structure comprises a substantially round protrusion extending proximally from the rotatable drive structure.

Example 19 relates to the device according to Example 18, wherein the second engagement structure comprises an engagement slot sized and shaped to receive the first engagement structure such that the first engagement structure is rotatable in relation to the linear drive shaft but is not moveable axially in relation to the linear drive shaft.

Example 20 relates to the device according to Example 17, wherein the distal member is movable radially and axially in relation to the proximal member via the slidable joint between an aligned position in which the longitudinal axis of the distal member is substantially coaxial with the longitudinal axis of the proximal member and an articulate position in which the longitudinal axis of the distal member is non-coaxial and parallel with the longitudinal axis of the proximal member.

While multiple embodiments are disclosed, still other embodiments of the disclosure will become apparent to those skilled in the art from the following detailed description, which shows and describes illustrative embodiments. As will be realized, the disclosure is capable of modifications in various obvious aspects, all without departing from the spirit and scope of the present disclosure. Accordingly, the drawings and detailed description are to be regarded as illustrative in nature and not restrictive.

DETAILED DESCRIPTION

The various embodiments disclosed and contemplated herein relate to adjustable intramedullary fixation and/or fusion devices and related systems and methods. Each of the devices is configured such that the device can be adjusted after implantation into the target bone. The devices disclosed and contemplated herein are taught with reference to the fibula but may be implemented in various other bones as would be appreciated by those of skill in the art, including, for example, the ulna and other similar bones. Certain implementations can be used not only to correct fibular fractures and syndesmosis dislocations, but also to correct similar fractures in other, similar bones such as the ulna.

Figures 1A, 1B:
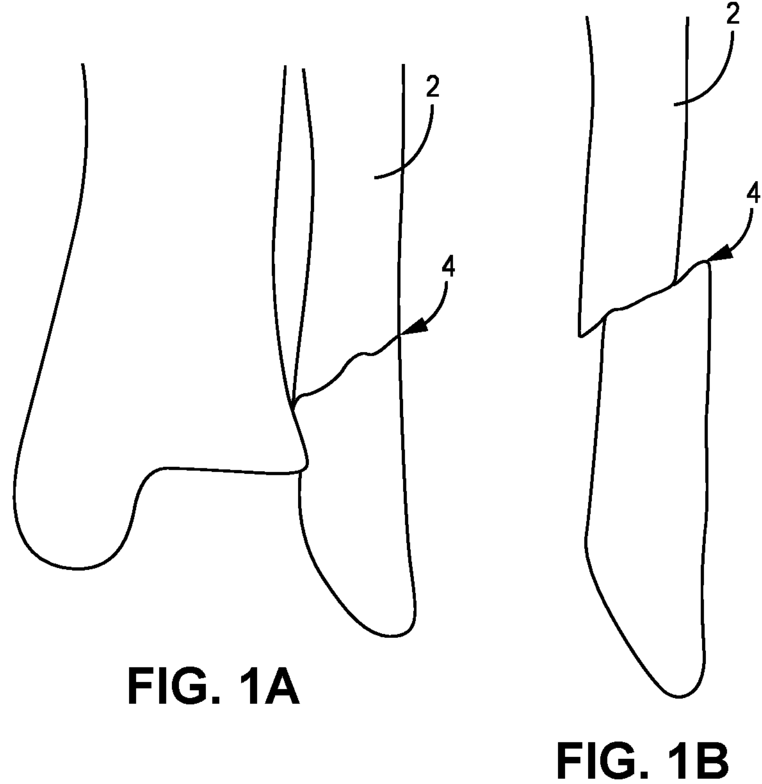
FIG. 1A is a schematic representation of a tibia and a fractured fibula.
FIG. 1B is a schematic representation of a displaced fibular fracture.

As shown in FIGS. 1A and 1B, in one exemplary bone fracture that can be treated by the various embodiments herein, the fibula 2 may be fractured or dislocated, requiring surgical intervention to reduce and stabilize the injury. A fibular fracture 4 (or any target bone fracture) may be non-displaced (as shown in FIG. 1A) or displaced (as shown in FIG. 1B). A displaced fracture 4 must be reduced and realigned to allow for proper healing. Known fixation devices allow for little or no ability to adjust the placement of the fixation device and/or reduce the fracture 4 after insertion of the fixation device. In contrast, the various fixation device implementations disclosed and/or contemplated herein have an adjustable joint such that they allow for adjustments after insertion of the fixation device.

Figure 2:
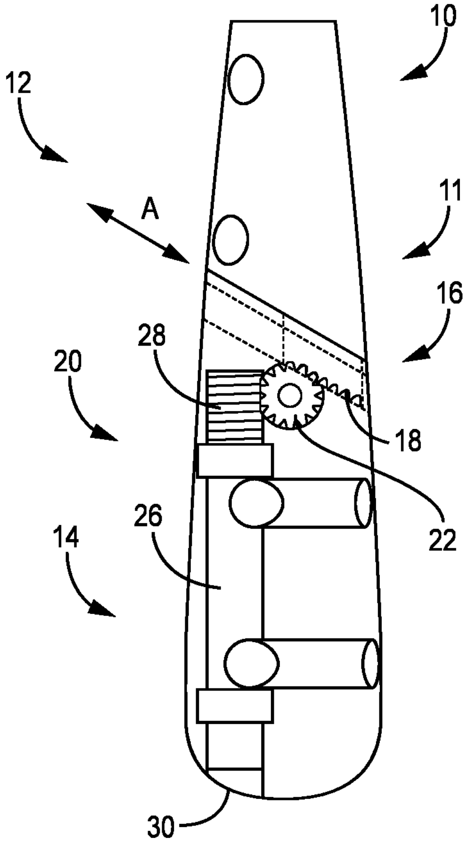
FIG. 2 is a side view of a fixation device, according to one implementation.
Figure 3:
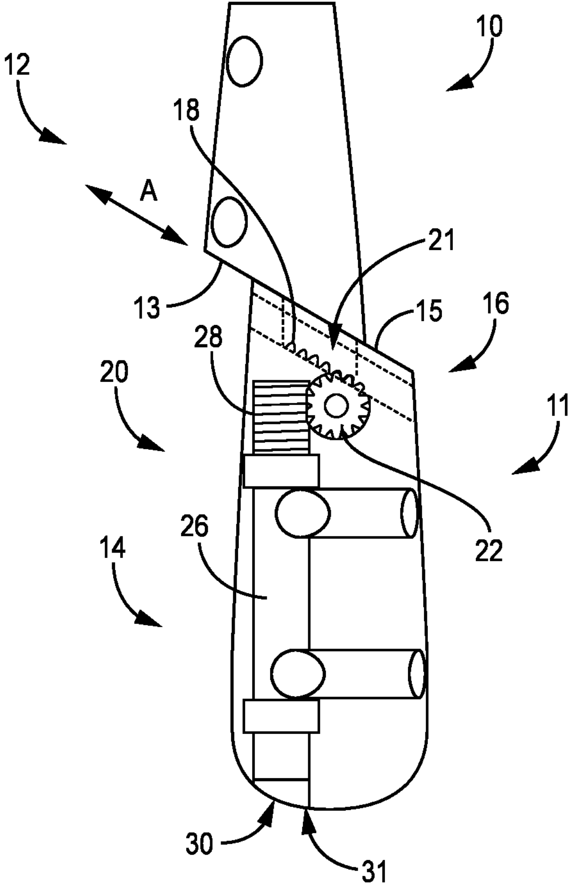
FIG. 3 is a further side view of the fixation device of FIG. 2 in the articulated position, according to one implementation.
Figure 4:
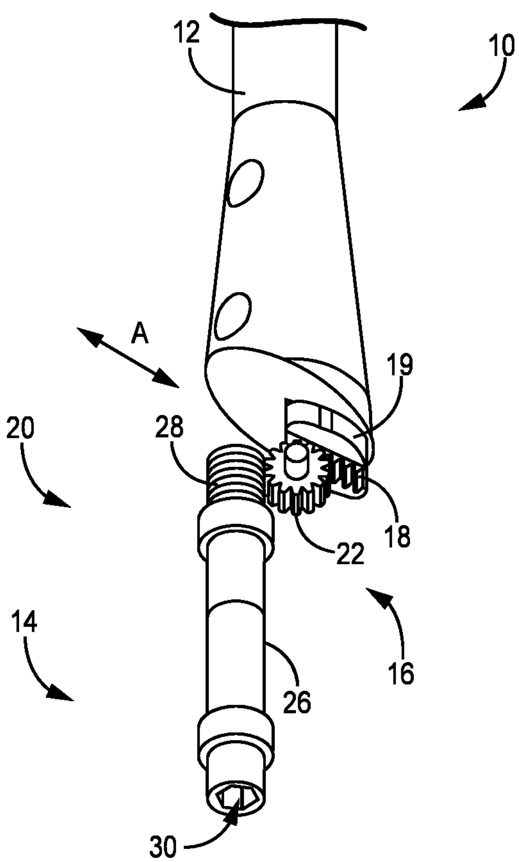
FIG. 4 is a bottom perspective view of a fixation device and drive mechanism with certain components removed for ease of viewing, according to one implementation.

As depicted in FIGS. 2-4 and 6A-7C, a bone fixation device (also referred to herein as a "nail" or "rod") 10, according to one implementation, is an elongate device that is placed within the medullary canal of the fibula 2 or other target bone for fixation of the bone after an injury. The device 10 has device body 11 with a proximal elongate section 12 and a distal elongate section 14. The two portions 12, 14 of the body 11 are adjustably coupled to each other at a joint 16. FIG. 2 depicts the device body 11 in the aligned position (also referred to herein as an "insertion position"), while FIG. 3 shows the device body 11 in an articulated position, and FIG. 4 shows a close up view of the joint (also referred to as an "adjustment mechanism") 16.

The two sections 12, 14 of the body 11 are identified as the proximal section 12 and the distal section 14 based on the positioning of the body 11 within the target bone and thus the resulting position of each of the sections 12, 14. That is, upon insertion into the target bone (as will be discussed below in detail with respect to FIGS. 7A and 7B), the proximal section 12 will be disposed toward the proximal end of the bone, while the distal section 12 will be disposed toward the distal end of the bone.

Figure 7A:
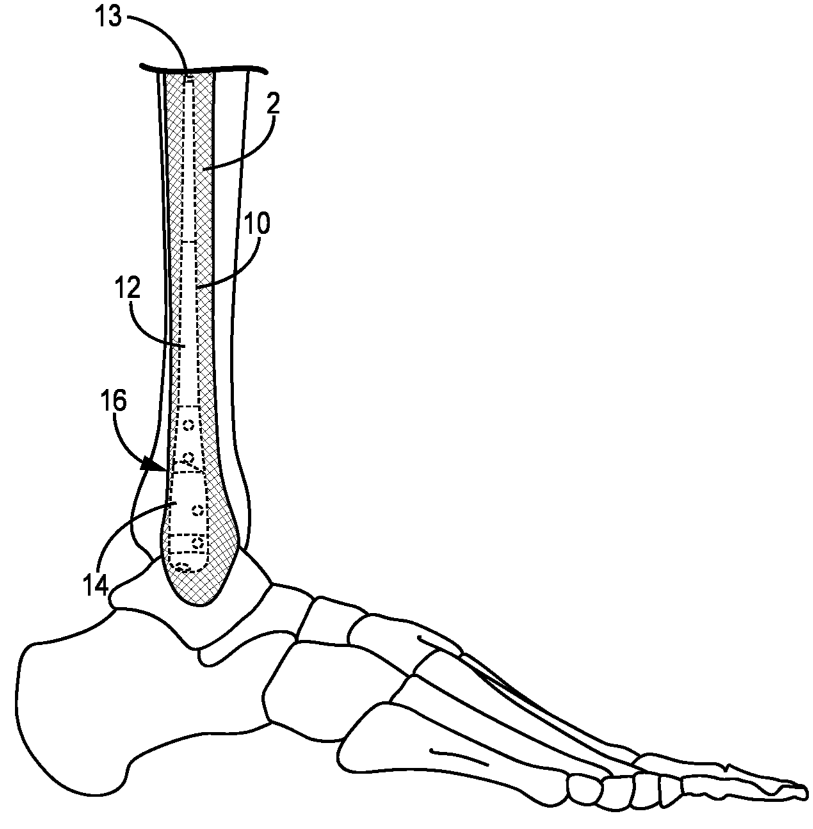
FIG. 7A is a lateral view of the fibula of a patient with an implanted fixation device, according to one implementation.
Figure 7B:
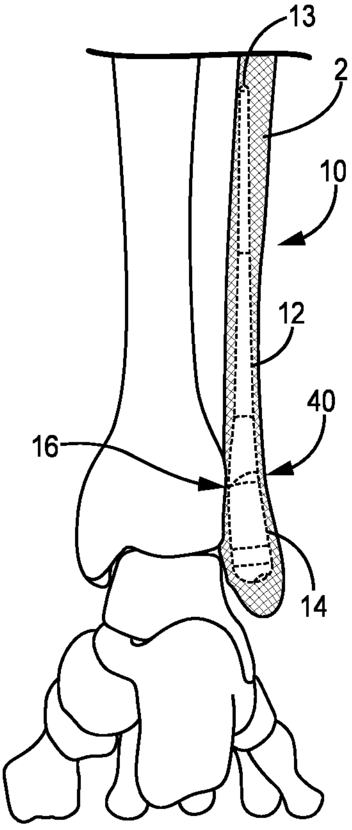
FIG. 7B is a posterior view of the fibula (and foot) of the patient of FIG. 7A with the implanted fixation device, according to one implementation.

As shown in FIGS. 7A and 7B, the proximal portion (also referred to as a "first shaft," "proximal member," "proximal shaft," "proximal pin," or "first rod") 12 of the device body 11 is an elongate structure having a blunted tip 13 at the proximal end for facilitating insertion into the medullary canal. As best shown in FIGS. 2-4, the distal end of the proximal shaft 12 forms a joint 16 with the proximal end of the distal shaft 14. The distal portion (also referred to as a "second shaft," "distal member," "distal shaft," "distal pin," or "second rod") 14 is coupled at its proximal end to the proximal portion 12 via the joint 16. The joint 16 is arranged such that the proximal portion 12 and distal portion 14 may move in relation to each other through the joint 16, in the direction of reference arrow A, which is substantially transverse to a longitudinal axis of the device body 11. That is, a drive mechanism 20 is provided that can actuate the two shafts 12, 14 to move substantially radially in relation to each other at the joint 16.

In the specific embodiment depicted herein, the joint 16 is configured as follows. The distal end of the proximal shaft 12 has a mateable mechanism or feature 18 disposed thereon that is mateably and moveably coupled with a driven gear (also referred to herein as a "cam drive" or "worm") 22 on the proximal end of the distal shaft 14 as shown. In one exemplary implementation as shown, the mateable mechanism 18 is a plurality of grooves 18 that can mateably couple with the threads or teeth of the driven gear 22 such that rotation of the gear 22 causes movement of the mateable mechanism 18 (and thus the proximal shaft 12). Alternatively, the mateable mechanism 18 can be any known structure, feature, or mechanism that can mateably couple with the driven gear in a similar fashion, including teeth, threads, etc. Further, the driven gear 22 can be any known type of gear, and thus can have any type of mateable structure that can mateably couple with the mateable mechanism or structure 18 such that rotation of the gear 22 can cause movement of the mechanism 18.

As best shown in FIG. 4, according to one specific implementation, the mateable mechanism or structure 18 is disposed or formed on a projection 19 that is disposed on the distal end of the proximal shaft 12. Alternatively, the mechanism 18 can be disposed or formed directly on the distal end of the proximal shaft 12. In addition, in certain embodiments including the device depicted in FIG. 4, the driven gear 22 is disposed at a position some distance distal from the proximal end of the distal shaft 14. That is, the proximal end of the distal shaft 14 has a channel 21 defined therein such that the threads or teeth of the gear 22 are disposed within the channel 21. In such implementations, the projection 19 of the proximal shaft is disposed within the channel 21 such that the mateable mechanism or structure 18 on the projection 19 is coupled with the teeth or threads of the gear 22. According to certain embodiments, the projection 19 has a coupling mechanism that slidably mates with and couples to a coupling mechanism associated with the channel 21, thereby ensuring that the two shafts 12, 14 remain coupled together while the drive mechanism 20 moves the two shafts 12, 14 in relation to each other as described herein.

The drive mechanism 20 disposed in the distal shaft 14 is made up of a drive shaft 26 and the rotatable driven gear 22, wherein the shaft 26 is rotatably coupled to the gear 22 at the mateable mechanism or structure 28 disposed at or near the proximal end of the shaft 26. In one embodiment, the mateable mechanism or structure 28 is a set of threads 28. Alternatively, any known mateable mechanism or structure that can mate with the gear 22 can be used. Thus, the gear 22 is operably coupled with both the mateable mechanism or structure 18 of the proximal portion 12 and the mateable mechanism or structure 28 of the drive shaft 26 such that rotation of the drive shaft 26 causes rotation of the mateable mechanism or structure 28, which thereby actuates the gear 22 to rotate on a different axis in comparison to the axis of the drive shaft 26. Actuation of the driven gear 22 causes the gear 22 to rotate, thereby mateably coupling with the mateable mechanism or structure 18 of the proximal portion 12 and urging the mateable mechanism or structure 18, and thus the distal shaft 14, to move angularly relative to proximal shaft 12 in the direction of reference arrow A. That is, in accordance with certain implementations, the actuation of the drive mechanism 20 causes the distal shaft 14 to move relative to the proximal shaft 12 because the proximal shaft 12 is securely disposed within a proximal portion of the medullary canal of the target bone such that the proximal shaft 12 cannot move in relation to the target bone. That is, in certain target bones (such as, for example, the fibula), the medullary canal of the proximal portion of the bone is narrower than the canal of the distal portion. Thus, when the device 10 is positioned within the medullary canal of the target bone, the proximal shaft 12 is disposed within the narrower portion of the medullary canal such that the shaft 12 cannot move radially in relation to the target bone (or can only move radially a small distance). Alternatively, either or both of the proximal shaft 12 or the distal shaft 14 can move in relation to the other.

As best shown in FIG. 3, according to certain implementations, regardless of the drive mechanism incorporated into the device 10, the distal end 13 of the proximal shaft 12 and the proximal end 15 of the distal shaft 14 are angled. That is, the two ends 13, 15 of the two shafts 12, 14 are each disposed at an angle as shown to create an angular movement when the drive mechanism 20 is actuated to move the two shafts 12, 14 in relation to each other. More specifically, the distal end 13 of the proximal shaft 12 is disposed at an angle in relation to the longitudinal axis of the shaft 12 that is not perpendicular to that axis. Similarly, the proximal end 15 of the distal shaft 14 is disposed at an angle that is parallel to and mateable with the angle of the distal end 13 of the proximal shaft 12 such that the two ends 13, 15 can be mateably coupled or disposed in moveable contact with each other as shown. Further, the threads 18 are disposed at the same angle or parallel to the angle of the two ends 13, 15. It is understood that the angular disposition of two ends 13, 15 as shown allows for both radial and axial movement of the two shafts 12, 14 in relation to each other. This angular movement both radially and axially can provide for adjustment of the fracture to align the two unaligned lengths of bone both radially and axially as desired. Further, in this device 10 and any of the various embodiments herein, the ends 13, 15 can have different angles than those depicted in FIG. 3. That is, the joint angle (the matching angle of the two ends 13, 15) can be altered to obtain the optimal amount of axial vs. radial movement. If it is desirable to have equal axial and radial movement, then the angle can be set at 45°. Alternatively, if it is desirable to have more axial movement than radial movement, then the angle can be set to accomplish that. And similarly, if it desirable to have more radial movement than axial movement, then the angle can be set to accomplish that. It is understood that any angle between 0° and 90° can be used for any of the various device implementations disclosed or contemplated herein. Alternatively, the angle can range from about 20° to about 70°. In a further alternative, the angle can range from about 30° to about 60°. In yet another alternative, the angle can range from about 0° to about 30°.

In addition, the drive shaft 26 can extend to the distal end of the distal shaft 14 and have a connection component 30 at its distal end that is accessible via an opening 31 in the distal end of the distal shaft 14 such that a driver tool can be coupled to the connection component 30. The connection component 30 can be an opening, a protrusion, or any mateable connection mechanism 30 that allows for a driver tool to be coupled thereto. For example, the mateable connection mechanism 30 in this specific embodiment is an opening 30 defined in the distal end thereof whereby a mechanical actuation component (also referred to herein as a "driver component," "hex driver," or "driver") (not pictured) may be inserted into the opening 30 to rotate the drive shaft 26. More specifically, the opening 30 has a hexagonal shape (or any known mateable and actuable shape) that is mateable with the distal end of the driver (not shown) such that the driver can be used to rotate the shaft 26 via the hexagonally shaped opening 30. Alternatively, the distal end of the drive shaft 26 can have any known coupling mechanism or connection component that can mateably couple with an appropriate corresponding driver tool. The drive tool can used by a user (such as a surgeon) to actuate the drive mechanism 20 to adjust the joint 16. More specifically, rotation of the connection mechanism 30 (via a tool) causes rotation of the drive shaft 26, which causes rotation of the gear 22, thereby causing adjustment of the position of the proximal shaft 12 in relation to the distal shaft 14.

Figure 5A:
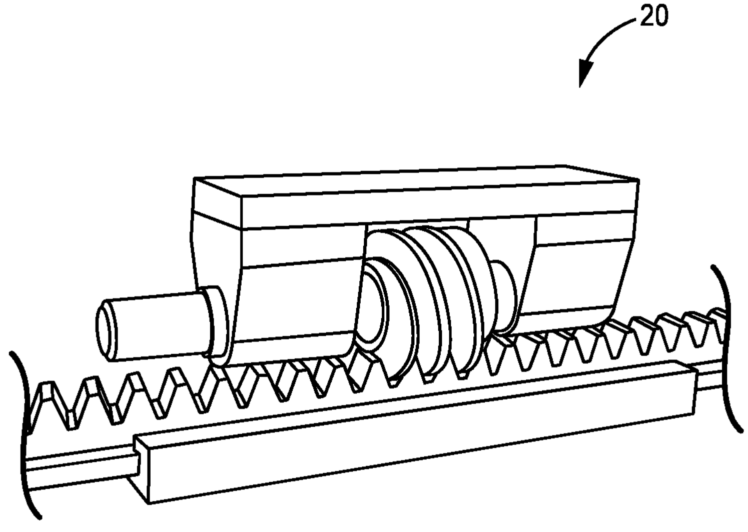
FIG. 5A depicts an exemplary rack and worm drive mechanism for incorporation into any of the embodiments herein, according to one embodiment.
Figure 5B:
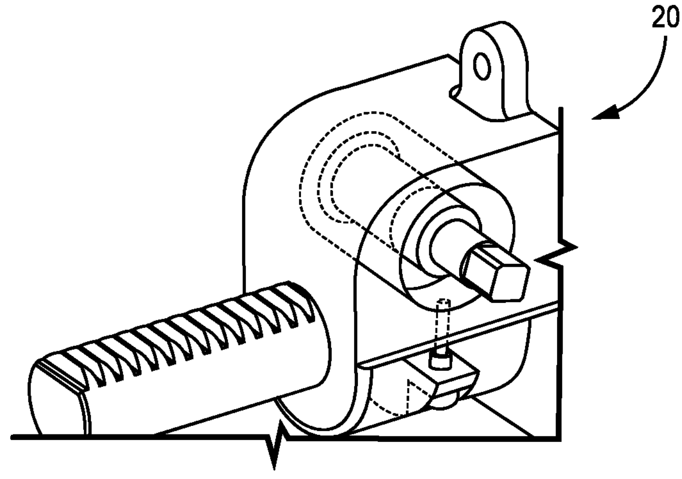
FIG. 5B depicts another exemplary rack and pinion drive mechanism for incorporation into any of the embodiments herein, according to a further embodiment.

It is understood that any other known drivers and similar mechanisms for use in medical devices can be used in place of the drive mechanism 20 as shown in FIGS. 2-4. For example, as depicted in FIGS. 5A and 5B, various other drive mechanisms 20 may be used in conjunction with the device 10. In one example, a rack and worm mechanism 20 as shown in FIG. 5A may be implemented. In another example, a rack and pinion or gear drive 20 as shown in FIG. 5B may be implemented.

As shown in 6A-6B, in certain implementations, the device 10 may also include one or more apertures 32, 34 for the insertion of locking screws, syndesmotic screws, or other similar, known fixation devices. The various screws or other types of known mechanisms may be disposed through the apertures 32, 34 within the device 10 to secure the device 10 in relation to the target bone of the patient and reduce instability. For example, proximal apertures 32 are disposed within the proximal shaft 12 and allow for angular placement of a syndesmotic screw or other screw across the syndesmosis and into the tibia. The distal apertures 34 are provided for fixation of the distal shaft 14 of the device 10 within the bone.

Figures 6A, 6B:
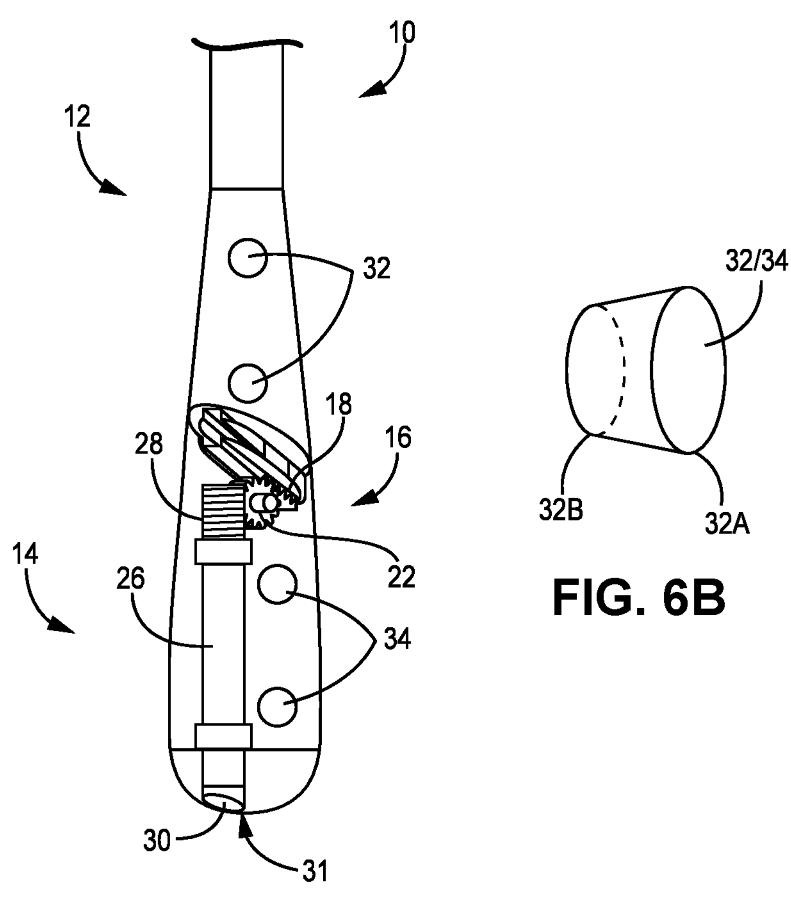
FIG. 6A is a side view of a fixation device, according to another implementation.
FIG. 6B is a side view of an exemplary aperture of the fixation device of FIG. 6A, according to one implementation.

In some implementations, each of the apertures 32, 34 are arranged in the shape of a frustum, as best shown in the exemplary depiction of one such aperture 32, 34 in FIG. 6B. In these implementations, the medial portion of the aperture 32A is wider than the lateral portion of the aperture 32B. It is understood that various other configurations and shapes are possible.

In some implementations, the device 10 may be made of one or more metals. For example, the device 10 may be made of titanium, stainless steel, or other appropriate metal material or combination of metal materials as would be appreciated by those of skill in the art. Alternatively, the device 10 can be made of any known material for use in bone fixation and/or other medical devices.

It is understood that the device 10 may be of various sizes and shapes as necessary for the particular anatomy of the target bone, medullary canal, fracture, and patient. Various lengths and widths of the device 10 may be used.

Figure 7C:
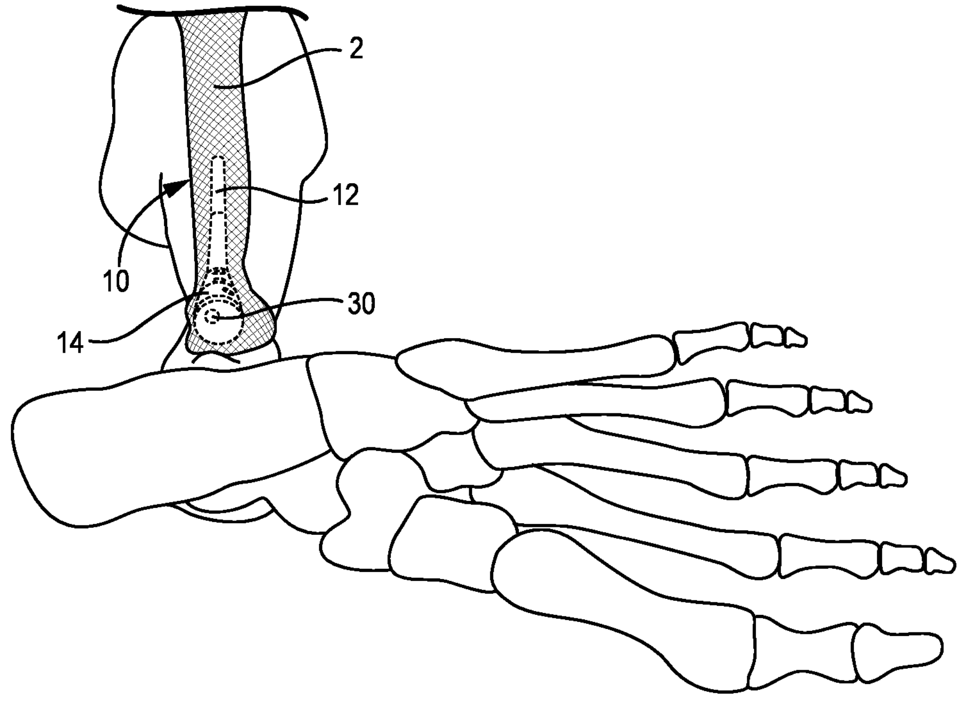
FIG. 7C is a bottom perspective view of the foot and fibula of the patient of FIG. 7A with the implanted fixation device, according to one implementation.

In use, as depicted in FIGS. 7A-7C, a fixation device 10—according to any embodiment disclosed or contemplated herein—may be placed within the medullary canal of the fibula 2 or other target bone via any appropriate surgical technique. For example, other target bones can include, but are not limited to, the humerus, tibia, femur, or any other long bone. In some implementations, the distal portion 14 has a bend (also referred to as "an angle" or "a curve") 40 as best shown in FIG. 7B that is intended to substantially replicate the bend or curve of the target fibula 2 and thereby ensure intramedullary placement. In various implementations, the bend 40 is about a 7° bend. Alternatively, depending on the target bone and any curvature thereof, any known angle that improves placement of the device 10 can be used. Of course, other shapes are possible.

In one example, the device 10 is inserted by drilling a pilot hole in the distal end of the fibula 2 of the patient. A guidewire may then be inserted into the medullary canal through the pilot hole and a hole drilled over the guidewire. The device 10 may be inserted within the hole within the medullary canal of the fibula 2. Of course, various other techniques and methods may be used, as would be appreciated by those of skill in the art.

An external targeting apparatus (not shown) may be used to assist in accurate and reproducible placement of the device 10 and/or screws. The external targeting apparatus may be disposed external to the fracture 4. It is understood that various targeting apparatuses are known in the art.

In various implementations, the device 10 should be placed within the fibula 2 or other target bone such that the joint 16 is substantially adjacent to the fracture 4. After the device 10 is placed within the fibula or other target bone, the drive mechanism 20 can be engaged to actuate the joint 16 to move the two shafts 12, 14 in relation to each other and thereby reduce the fracture 4 and realign the bone. The ability to actuate the proximal portion 12 relative to the distal portion 14 (and/or vice versa) after insertion allows a surgeon or other user to make corrections and adjustments to the bone alignment and fracture reduction after implantation of the device 10. The device 10 is placed within the bone and actuated such as to hold the bone in proper alignment during the healing process. Improved reduction of a fracture and proper bone alignment may lead to faster healing and better outcomes for patients.

Figures 8A, 8B:
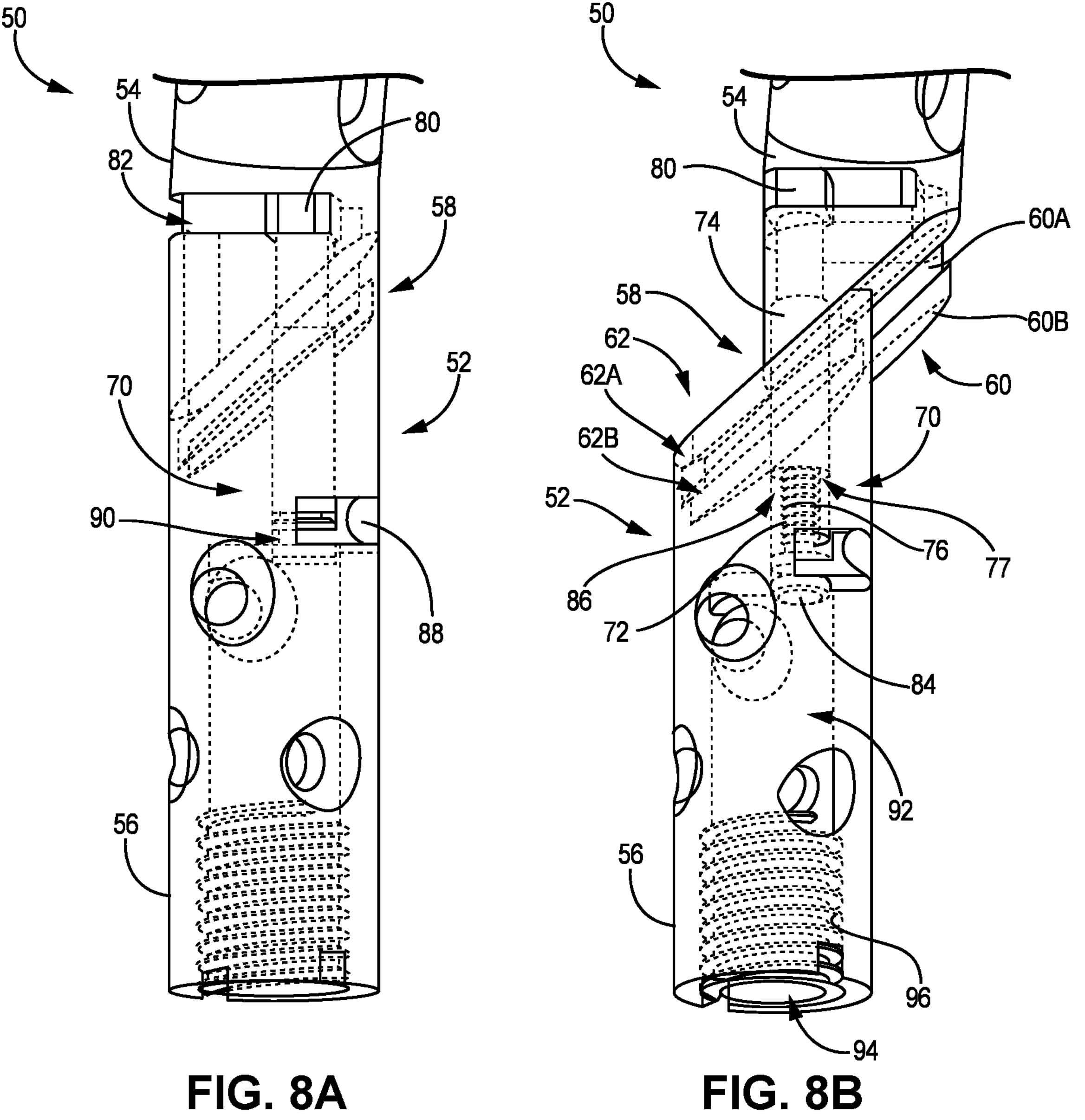
FIG. 8A is an expanded side view of a portion of a fixation device, according to another embodiment.
FIG. 8B is a further expanded side view of the portion of the fixation device of FIG. 8A in the articulated position, according to one embodiment.

Another embodiment of a fixation device 50 is depicted in FIGS. 8A and 8B, which provide expanded views of the drive mechanism 70 and joint 58 of the device 50. Except as expressly discussed herein, the various components and features of this device 50 embodiment are substantially similar or identical to the components and features of the various embodiments disclosed or contemplated above and depicted in FIGS. 2-7C. In this implementation, the device 50 has a device body 52 with a proximal elongate section 54 and a distal elongate section 56 that are adjustably coupled to each other at the joint 58 such that the drive mechanism 70 can cause the two sections 54, 56 to move substantially radially in relation to each other. FIG. 8A depicts the device body 52 in the aligned (or "insertion") position or configuration, while FIG. 8B shows the device body 52 in an articulated position or configuration.

It should be noted that in all of the various embodiments herein, the "aligned" or "insertion" configuration describes the device body (in this specific case, body 52), not the condition of the target bone. That is, when the device 50 (or any device implementation herein) is inserted into the target bone, the device body 52 is aligned, but the target bone is misaligned (fractured). Similarly, when the device body (such as body 52) is urged into its articulated configuration (such as the configuration depicted in FIG. 8B, for example), that is when the target bone is intended to be corrected and thus urged into alignment (to treat the fracture).

Further, it should also be noted that in most implementations, when the device is inserted into the target bone, the proximal section of the various device embodiments herein (such as section 54) is positioned within the bone such that the proximal section 54 is substantially immovable. As such, the relative movement of the proximal and distal shafts (such as proximal 54 and distal 56 shafts in this embodiment) as discussed with respect to the various implementations herein generally involves movement of the distal shaft in relation to the proximal shaft.

In this exemplary embodiment, the joint 58 is configured as follows. As best shown in FIG. 8B, the distal end of the proximal shaft 54 has a mateable mechanism or feature 60 disposed thereon that is mateably and moveably coupled with a mateable mechanism 62 disposed on the proximal end of the distal shaft 56 as shown. More specifically, in this exemplary implementation the mateable mechanism 60 is two elongate protrusions (or "ribs") 60A, 60B and the mateable mechanism 62 is two corresponding channels 62A, 62B. As such, the two ribs 60A, 60B can be slidably positioned in and mateably couple with the two channels 62A, 62B such that the two protrusions 60A, 60B can slide within the two channels 62A, 62B. Alternatively, the mateable mechanisms 60, 62 can be any known structures, features, or mechanisms that can mateably and slidably coupled to allow for movement of the two shafts 64, 66 in relation to each other via the mateable mechanisms 60, 62.

The drive mechanism 70 disposed in the distal shaft 56 (and operably coupled to the proximal shaft 54) is made up of a rotatable drive screw 72 rotatably coupled to a linear driven shaft 74. More specifically, the drive screw 72 has external threads 76 defined thereon and is rotatably disposed within a lumen 78 defined within the driven shaft 74. The lumen 78 has matching threads (not shown) defined on an inner surface of the lumen 78. As such, rotation of the drive screw 72 within the lumen 78 causes linear or axial movement of the driven shaft 74. The driven shaft 74 has a slidable block 80 at its proximal end that is slidably disposed within a radial slot 82 defined within the proximal shaft 54 such that the block 80 can slide within the slot 82. In addition, the drive screw 72 has a mateable connection component 84 defined or otherwise disposed at the distal end of the drive screw 72. The mateable connection component 84 can be any known mateable structure or mechanism 84 for receiving or coupling with a drive tool (not shown) such that the tool can be used to rotate the screw 72.

In the distal shaft 56, the drive screw 72 and driven shaft 74 are moveably disposed within a first axial lumen (or "drive mechanism lumen") 86 defined within the distal shaft 56. Further, as best shown in FIG. 8A, a retention structure (or "retainer" or "protrusion") 88 is positioned adjacent to and coupled with the drive screw 72 such that the protrusion 88 is disposed within a channel 90 defined in the screw 72.

As such, the protrusion 88 allows the screw 72 to rotate but prevents the screw 72 from moving axially.

The distal shaft 56 also has a second axial lumen (or "drive tool lumen") 92 that extends from the distal end of the shaft 56 to the first lumen 86. Further, the distal shaft 56 has an opening 94 at the distal end that is in fluidic communication with the lumen 92. As such, a drive tool (such as a wrench or any other known tool) can be inserted into the lumen 92 and coupled with the drive screw 72 at the connection component 84 when a user or surgeon wants to use the drive screw 72 to adjust the positioning of the distal 56 and proximal 54 shafts in relation to each other.

In certain implementations, a distal portion of the drive tool lumen 92 can have threads 96 defined in an inner surface of the lumen 92. The threads 96 can be used to mateably couple with a cap or plug (not shown) that can be inserted into the lumen 92 and mateably coupled to the threads 96 to provide a closure or covering for the lumen 92. Alternatively, any mateable mechanism or structure 96 can be incorporated therein. Such a cap or other covering structure can be used with any of the device embodiments disclosed or contemplated herein. According to some embodiments, the cap or other covering structure is used to cover the opening 94 and lumen 92 to prevent any bone ingrowth therein. The cap or other structure can be attached to the distal end of the distal shaft 56 either before or after the device 50 is implanted and can be removed if a user or surgeon wants to access the lumen 92 to actuate the drive mechanism 70.

In a further alternative, the threads 96 in this embodiment (and in any other implementation herein) can also be used for removal of the device 50. That is, if it is desirable to extract or otherwise remove the device 50 from the target bone, the cap as discussed above can be removed (if the cap was previously attached) and a removal tool (not shown) with external threads on its outer surface can be inserted into the lumen 92 and threadably coupled to the threads 96 within the lumen 92. Once the removal tool is attached to the distal shaft 56 via the threads, the tool can then be used to remove the device 50 from the bone.

In use according to various implementations, the device 50 is placed within a fibula or other target bone such that the joint 58 is substantially adjacent to the fracture. After the device 50 is placed within the fibula or other target bone, the drive mechanism 70 can be engaged to actuate the joint 58 to move the two shafts 54, 56 in relation to each other and thereby reduce the fracture and realign the bone. More specifically, a drive tool (not shown) is inserted into the drive tool lumen 92 and coupled with the drive screw 72 at the connection component 84. Once the drive tool is coupled to the drive screw 72, the tool can be used to rotate the drive screw 72, thereby causing the driven shaft 74 to move axially in one direction or the other, which causes the proximal shaft 54 to move radially in one direction or the other in relation to the distal shaft 56. For example, the device 50 can initially be disposed in the insertion configuration as shown in FIG. 8A. The drive tool can then be used to rotate the drive screw 72 such that the driven shaft 74 moves axially in the proximal direction. This causes the block 80 to move in the proximal direction, which, as shown in FIG. 8B, urges the distal shaft 56 to move distally and radially along the joint 58 via the slidable ribs 60A, 60B as discussed above. And as the distal shaft 56 moves radially (to the "left" as shown in FIG. 8B) and axially ("down" as shown in FIG. 8B), the block 80 moves only radially in relation to the proximal shaft 54 such that the position of the block 80 changes within the slot 82 as shown. Alternatively, in certain embodiments, the proximal shaft 54 can move in relation to the distal shaft 56, or both shafts 54, 56 can move in relation to each other.

Figures 9A, 9B:
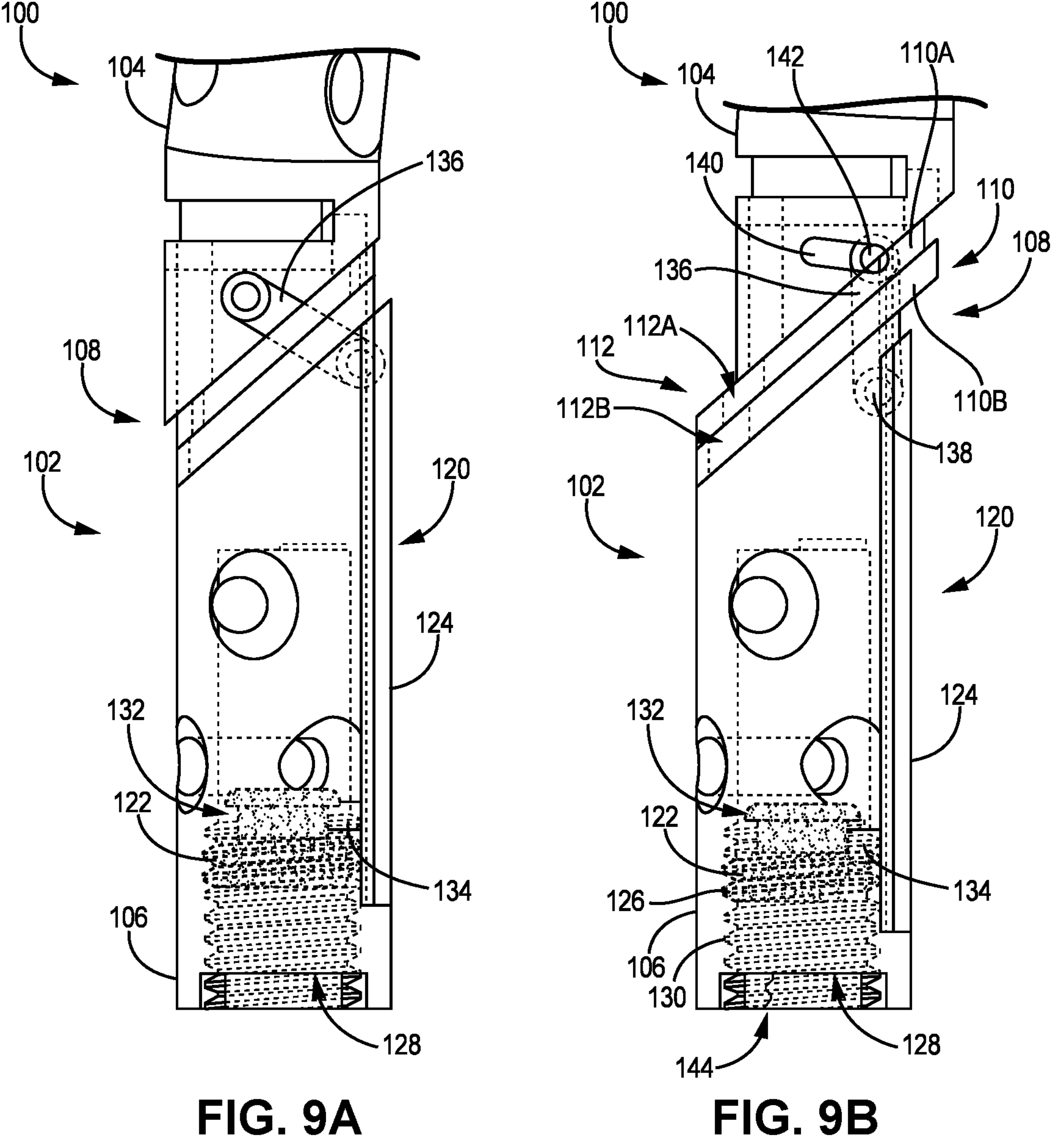
FIG. 9A is an expanded side view of a portion of another fixation device, according to a further embodiment.
FIG. 9B is a further expanded side view of the portion of the fixation device of FIG. 9A in the articulated position, according to one embodiment.

A further implementation of a fixation device 100 is depicted in FIGS. 9A and 9B, which provide expanded views of the drive mechanism 120 and joint 108 of the device 100. Except as expressly discussed herein, the various components and features of this device 100 embodiment are substantially similar or identical to the components and features of the various embodiments disclosed or contemplated above and depicted in FIGS. 2-7C. In this implementation, the device 100 has a device body 102 with a proximal elongate section 104 and a distal elongate section 106 that are adjustably coupled to each other at the joint 108 such that the drive mechanism 120 can cause the two sections 104, 106 to move substantially radially in relation to each other. FIG. 9A depicts the device body 102 in the aligned position, while FIG. 9B shows the device body 102 in an articulated position.

In this exemplary embodiment, the joint 108 is configured as follows. As best shown in FIG. 9B, the distal end of the proximal shaft 104 has a mateable mechanism or feature 110 disposed thereon that is mateably and moveably coupled with a mateable mechanism 112 disposed on the proximal end of the distal shaft 106 as shown. More specifically, in this exemplary implementation the mateable mechanism 110 is two elongate protrusions (or "ribs") 110A, 110B and the mateable mechanism 112 is two corresponding channels 112A, 112B. As such, the two ribs 110A, 110B can be slidably positioned in and mateably couple with the two channels 112A, 112B such that the two protrusions 110A, 110B can slide within the two channels 112A, 112B. Alternatively, the mateable mechanisms 110, 112 can be any known structures, features, or mechanisms that can mateably and slidably coupled to allow for movement of the two shafts 104, 106 in relation to each other via the mateable mechanisms 110, 112.

The drive mechanism 120 disposed in or otherwise associated with the distal shaft 106 (and operably coupled to the proximal shaft 104) is made up of a rotatable drive screw 122 operably coupled to a linear driven shaft 124. More specifically, the drive screw 122 has external threads 126 defined thereon and is rotatably disposed within the drive mechanism lumen 128 defined within the distal shaft 106. The lumen 128 has matching threads 130 defined on an inner surface of the lumen 128. As such, rotation of the drive screw 122 within the lumen 128 causes linear or axial movement of the drive screw 122 and thus axial movement of the driven shaft 124. More specifically, the drive screw 122 has a channel 132 defined in the screw 122, and the driven shaft 124 has a protrusion 134 that extends into and is positioned within the channel 132. As such, rotation of the drive screw 122 causes axial movement of the screw 122 within the lumen 128 (as a result of the threads 126, 130), which causes axial movement of the protrusion 134, which causes axial movement of the driven shaft 124.

The driven shaft 124 is slidably disposed along a side of the distal shaft 106. Alternatively, the driven shaft 124 can be slidably disposed within an elongate lumen defined within the distal shaft 106. At or near its proximal end, the driven shaft 124 has a rotatable link 136 rotatably coupled to the driven shaft 124 at a rotatable joint 138. The rotatable link 136 is coupled at a first end to the rotatable joint 138 and is slidably coupled at a second end to the proximal shaft 104 at a slot 140 defined in the proximal shaft 104 as shown. More specifically, the link 136 has a protrusion or rod 142 at the second end that is slidably disposed within the slot 140. Thus, axial movement of the driven shaft 124 causes some axial movement of the rotatable link 136 that is transferred by the link 136 to the proximal shaft 104. As the link 136 urges the proximal shaft 104 to move in relation to the distal shaft 106, the shaft 104 slides along the joint 108 as depicted in FIGS. 9A and 9B and as described in further detail elsewhere herein. And as the shaft 104 moves radially, the link protrusion 142 slides within the slot 140.

The distal shaft 106 has an opening 144 at the distal end that is in fluidic communication with the lumen 128. As such, a drive tool (such as a wrench or any other known tool) can be inserted into the lumen 128 and coupled with the drive screw 122 at a connection component (not shown) when a user or surgeon wants to use the drive screw 122 to adjust the positioning of the distal 106 and proximal 104 shafts in relation to each other.

In certain implementations, the threads 130 of the lumen 128 can be also used to mateably coupled with a cap or plug (not shown) that can be inserted into the lumen 128 and mateably coupled to the threads 130 to provide a closure or covering for the lumen 128 when no adjustment of the drive mechanism 120 is needed. Alternatively, any mateable mechanism or structure 130 can be incorporated therein. In a further alternative, the threads 130 in this embodiment (and in any other implementation herein) can also be used for removal of the device 100. That is, if it is desirable to extract or otherwise remove the device 100 from the target bone, a removal tool (not shown) with external threads on its outer surface can be inserted into the lumen 128 and threadably coupled to the threads 130 within the lumen 128. Once the removal tool is attached to the distal shaft 106 via the threads, the tool can then be used to remove the device 100 from the bone.

In use according to various implementations, the device 100 is placed within a fibula or other target bone such that the joint 108 is substantially adjacent to the fracture. After the device 100 is placed within the fibula or other target bone, the drive mechanism 120 can be engaged to actuate the joint 108 to move the two shafts 104, 106 in relation to each other and thereby reduce the fracture and realign the bone. More specifically, a drive tool (not shown) is inserted into the drive tool lumen 128 and coupled with the drive screw 122 at the connection component (not shown). Once the drive tool is coupled to the drive screw 122, the tool can be used to rotate the drive screw 122, thereby causing the drive screw 122 to move axially in one direction or the other, which causes the protrusion 134 to move axially in one direction or the other in relation to the distal shaft 106. This causes the driven shaft 124 to move axially in one direction or the other in relation to the distal shaft 106, which causes the rotatable link 136 to move axially, which causes the proximal shaft 104 to move axially and radially as described elsewhere herein along the joint 108. For example, the device 100 can initially be disposed in the insertion configuration as shown in FIG. 9A. The drive tool can then be used to rotate the drive screw 122 such that the driven shaft 124 moves axially in the distal direction. This causes the second end of the rotatable link 136 to move in a radial direction, which, as shown in FIG. 9B, urges proximal shaft 104 to move proximally and radially along the joint 108 via the slidable ribs 110A, 110B as discussed above. And as the protrusion 142 moves radially (to the "right" as shown in FIG. 9B), the proximal shaft 104 moves radially (and axially) to the "right" as well, as shown.

Figures 10A, 10B:
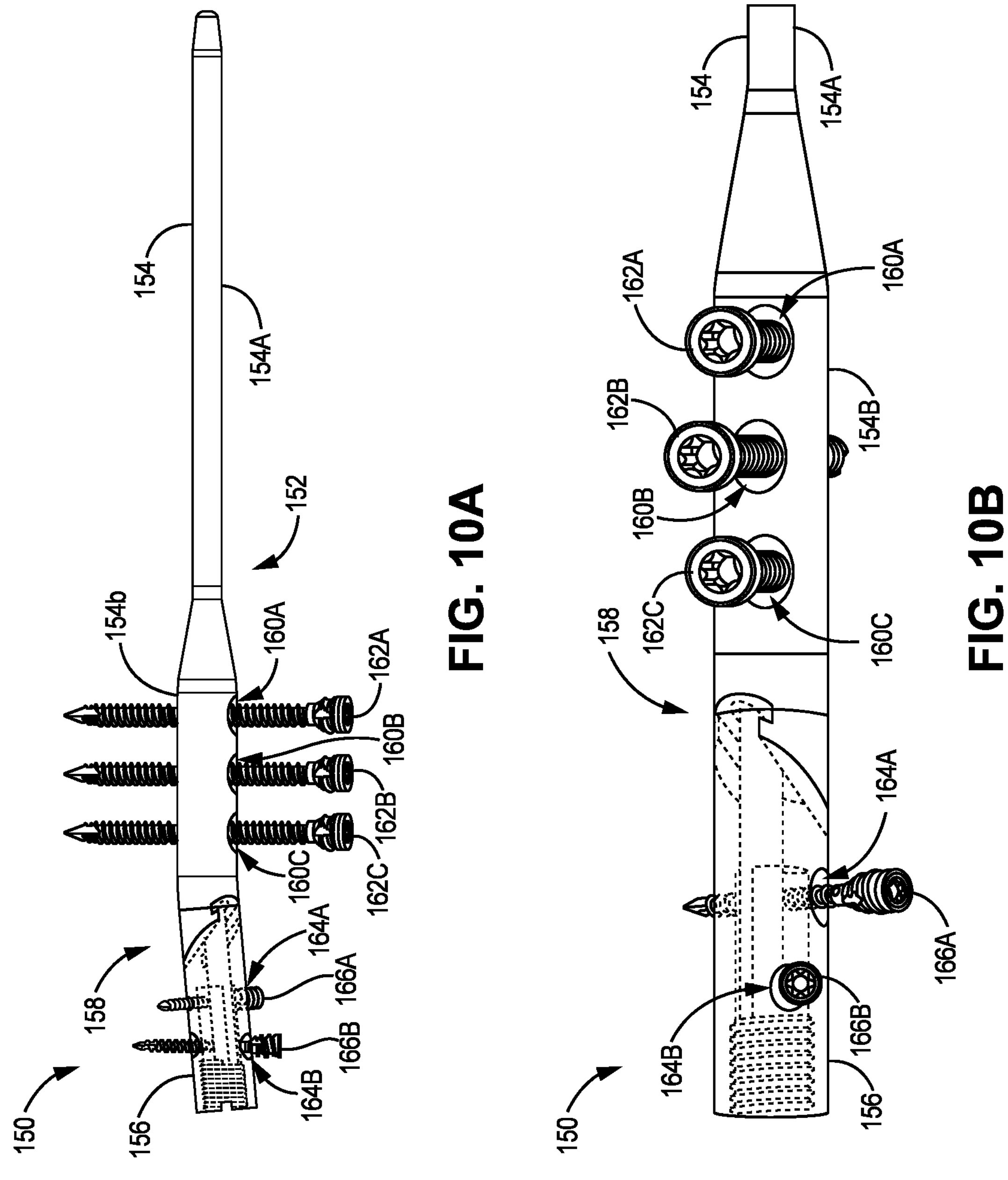
FIG. 10A is a side view of an entire fixation device in the aligned position, according to one implementation.
FIG. 10B is an expended side view of a portion of the fixation device of FIG. 10A, according to one embodiment.

FIGS. 10A and 10B depict another embodiment of a fixation device 150. More specifically, FIG. 10A depicts a view of the entire device 150, while FIG. 10B shows an expanded view of the distal shaft 156 and a distal portion of the proximal shaft 154 of the device 150. Except as expressly discussed herein, the various components and features of this device 150 embodiment are substantially similar or identical to the components and features of the various embodiments disclosed or contemplated above and depicted in FIGS. 2-9B. In this implementation, the device 150 has a device body 152 with the proximal elongate section 154 and the distal elongate section 156 that are adjustably coupled to each other at the joint 158 such that a drive mechanism (not shown) can cause the two sections 154, 156 to move substantially radially in relation to each other. The drive mechanism in this device 150 can be any of the drive mechanism implementations disclosed or contemplated above.

In this embodiment, the proximal shaft 154 has a proximal portion (or length) 154A and a distal portion 154B, wherein the distal portion 154B has a greater diameter than the proximal portion 154A. According to one embodiment, the distal portion 154B has a diameter ranging from about 0.5 mm to about 15 mm, while the proximal portion 154A has a diameter ranging from about 2 mm to about 4 mm. Further, the distal portion 154B has three lumens 160A, 160B, 160C defined therein, each of which is configured to receive a fixation screw 162A, 162B, 162C as shown or other similar mechanism. The greater diameter of the distal portion 154B makes it possible to have the three lumens 160A, 160B, 160C, thereby providing greater stability and fixation in comparison to known devices without such a distal portion and three such openings.

Each of the three openings 160A-C have an axis that is substantially transverse to the longitudinal axis of the proximal shaft 154 (and the distal portion 154B). In one embodiment as shown, all of the axes of the three lumens 160A-C are substantially parallel to each other. Alternatively, the axes of the three openings 160A-C are not parallel with each other. Further, in certain embodiments, the lumens 160A-C have no threads defined within the inner surfaces of the lumens 160A-C. In such implementations, the screws 162A-C (or other similar mechanisms), which can be threaded as shown, do not attach to the proximal shaft 154 via threads or any other mechanism and instead are simply disposed through the lumens 160A-C and attach to the bone through which the screws 162-C are disposed on either side of the shaft 154. Alternatively, the lumens 160A-C have threads defined therein.

The distal shaft, in certain embodiments, can also have lumens 164A, 164B defined therethrough, each of which is configured to receive a fixation screw 166A, 116B as shown or other similar mechanism. Each of the lumens 164A, 164B has an axis that is substantially transverse to the longitudinal axis of the distal shaft 146. In one embodiment as shown, the axes of the two lumens 164A, 164B are not parallel to each other. That is, the two lumens 164A, 164B are defined through the distal shaft 146 at different angles in relation to each other. Alternatively, the axes of the two lumens 164A, 164B can be substantially parallel with each other. Further, in certain embodiments, the lumens 164A, 164B have threads defined within the inner surfaces of the lumens 164A, 164B such that the screws 166A, 166B can mateably couple to the distal shaft 146 via the threads on the external surface of the screws 166A, 166B and the threads defined in the inner surfaces of the lumens 164A, 164B. Alternatively, the lumens 164A, 164B do not have threads defined therein.

Figures 11A, 11B:
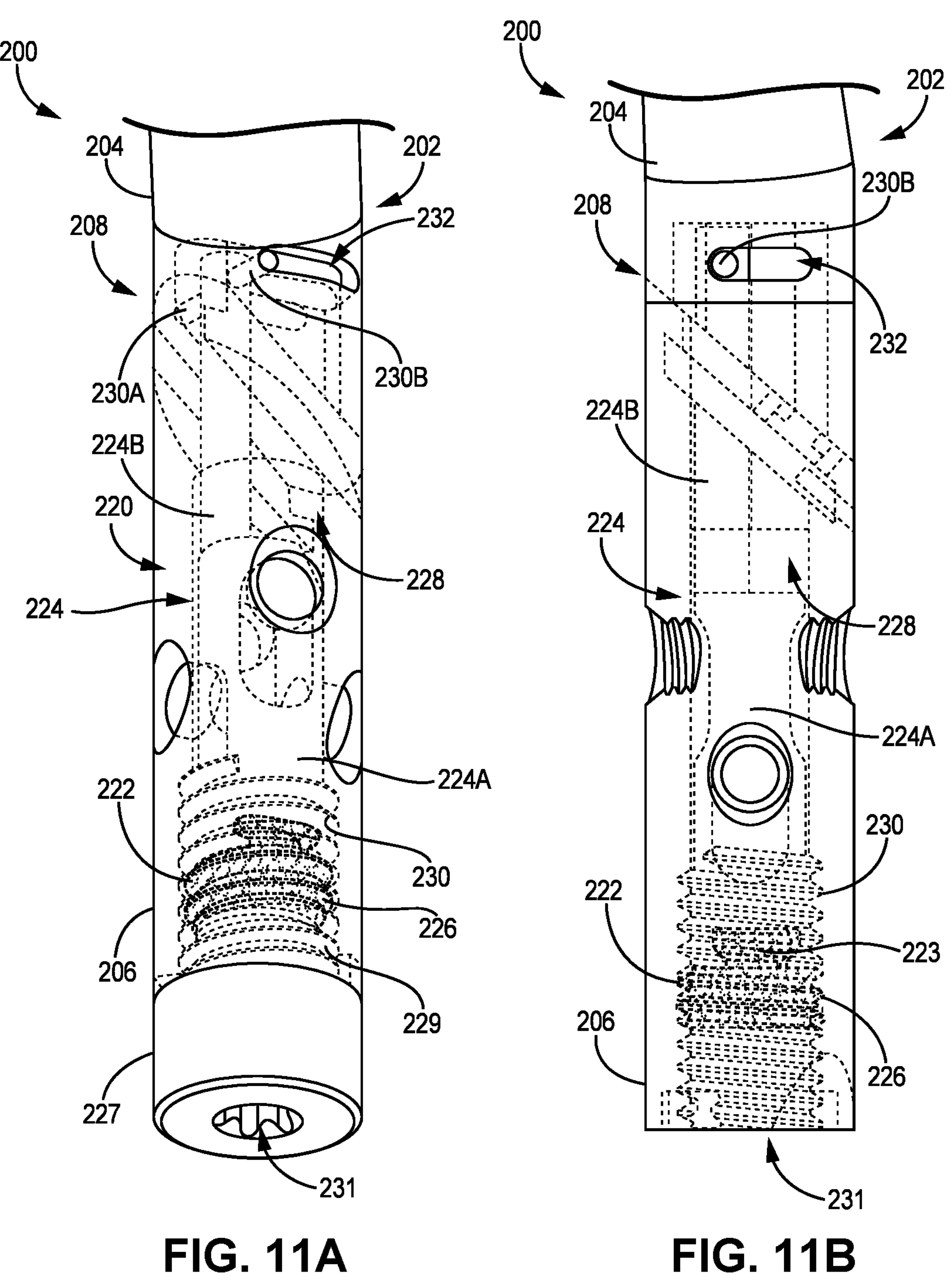
FIG. 11A is an expanded side view of a portion of another fixation device in the aligned position, according to a further embodiment.
Figures 11C, 11D:
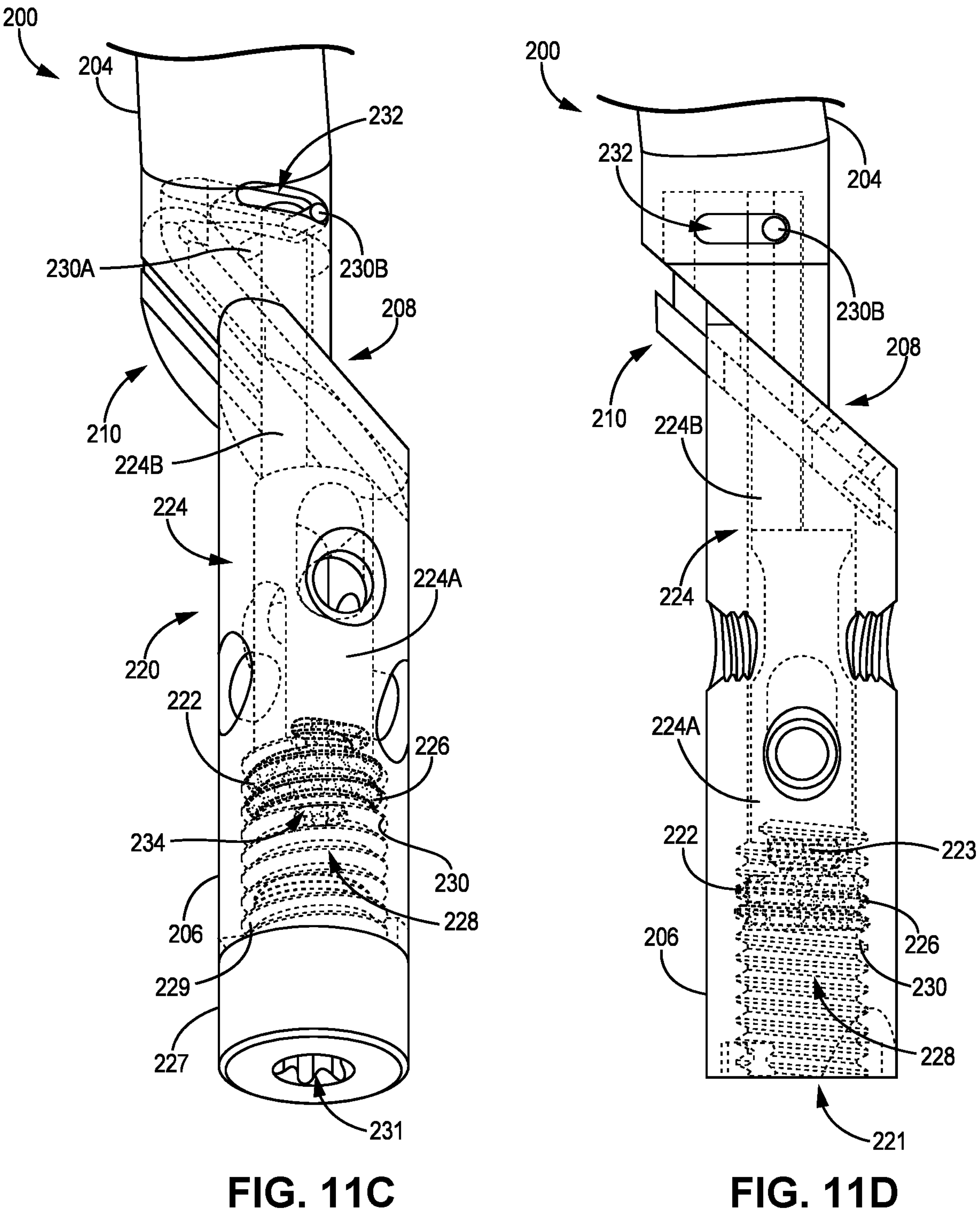
FIG. 11C is an expanded side view of the portion of the fixation device of FIG. 11A in the articulated position, according to one embodiment.
FIG. 11D is another expanded side view of the portion of the fixation device of FIG. 11A in the articulated position, according to one embodiment.

Another embodiment of a fixation device 200 is depicted in FIGS. 11A-120, with FIGS. 11A-11G depicting expanded views of the drive mechanism 220 and joint 208 of the device 200. Except as expressly discussed herein, the various components and features of this device 200 embodiment are substantially similar or identical to the components and features of the various embodiments disclosed or contemplated above and depicted in FIGS. 2-10B. In this implementation, the device 200 has a device body 202 with a proximal elongate section 204 and a distal elongate section 206 that are adjustably coupled to each other at the joint 208 such that the drive mechanism 220 can cause the two sections 204, 206 to move substantially radially in relation to each other. FIGS. 11A and 11B (along with FIGS. 11E and F) depict the device body 202 in the aligned (or "insertion") position or configuration, while FIGS. 11C and 11D shows the device body 202 in an articulated position or configuration.

Figures 12A, 12B, 12C:
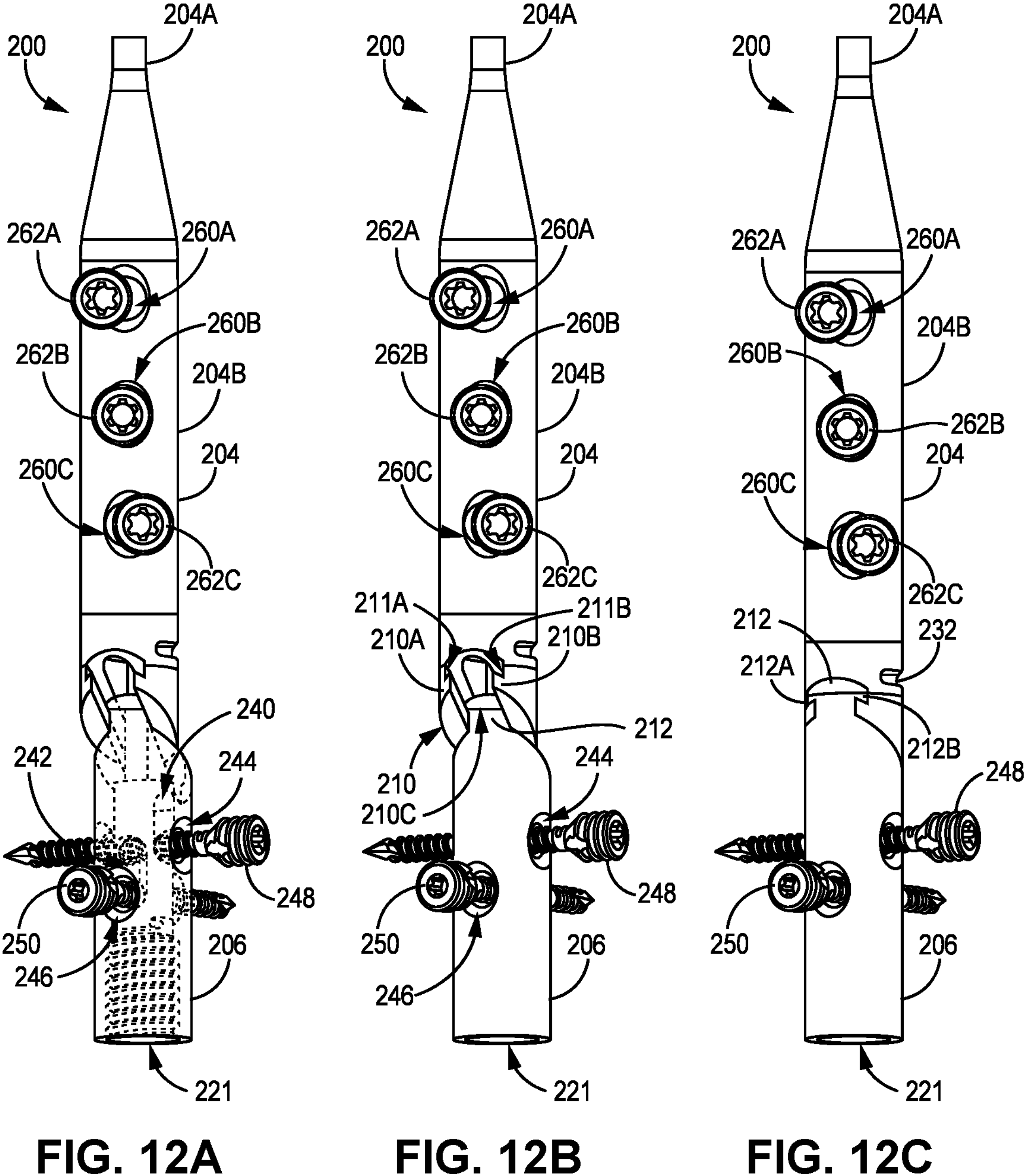
FIG. 12A is an expanded side view of a portion of another fixation device in the articulated position in which the internal drive mechanism is depicted, according to a further embodiment.
FIG. 12B is another expanded side view of the portion of the fixation device of FIG. 12A in the articulated position, according to one embodiment.
FIG. 12C is another expanded side view of the portion of the fixation device of FIG. 12A in the aligned position, according to one embodiment.
Figures 13A, 13B, 13C, 13D:
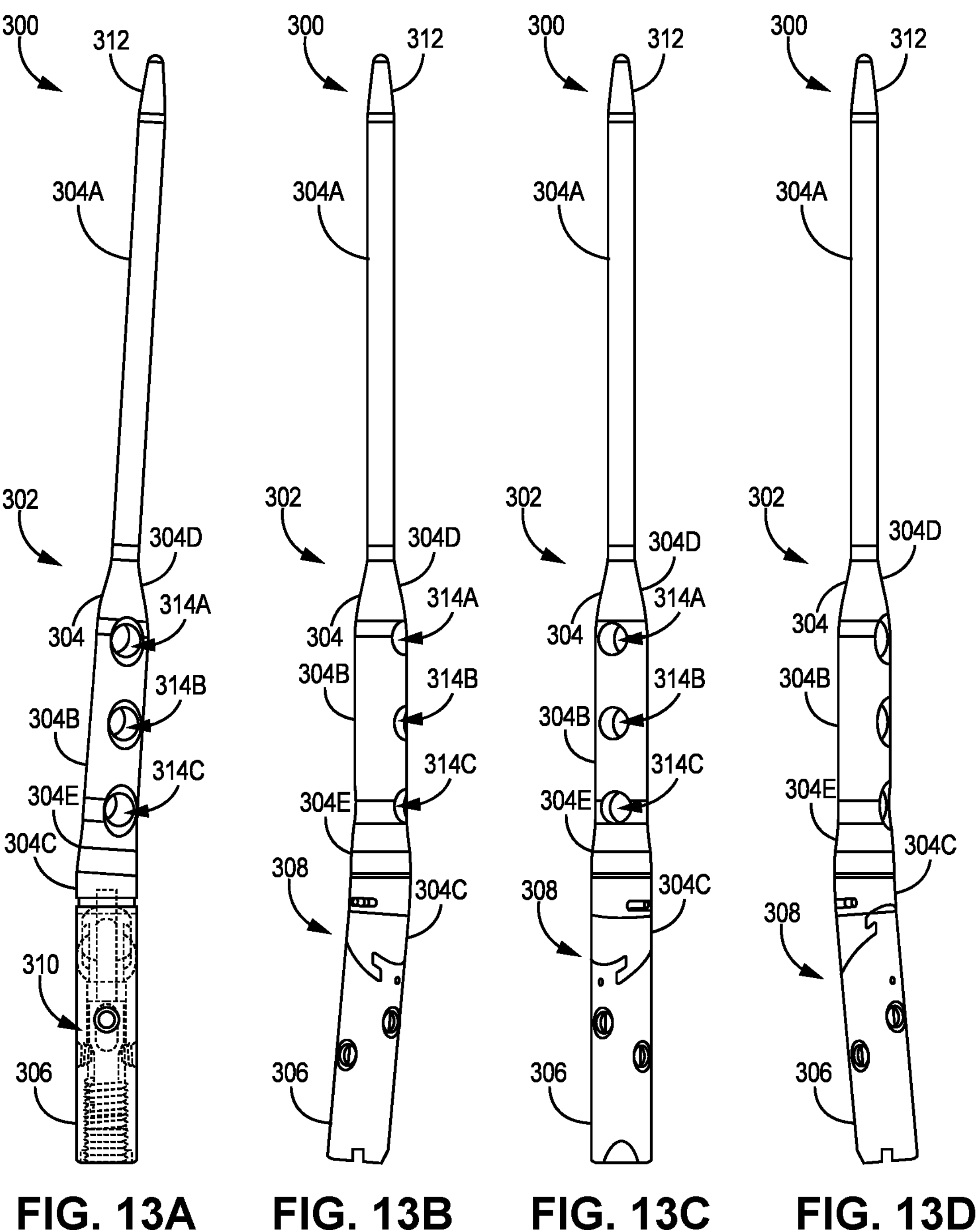
FIG. 13A is a side view of an entire fixation device in the aligned position in which the internal drive mechanism is depicted, according to a further embodiment.
FIG. 13B is another side view of the entire fixation device of FIG. 13A in the aligned position, according to one embodiment.
FIG. 13C is yet another side view of the entire fixation device of FIG. 13A in the aligned position, according to one embodiment.
FIG. 13D is an additional side view of the entire fixation device of FIG. 13A in the aligned position, according to one embodiment.

In this exemplary embodiment, the joint 208 is configured as follows. As best shown in FIGS. 11C, 11D, 12B, and 12C, the distal end of the proximal shaft 204 has a mateable mechanism or feature 210 disposed thereon that is mateably and moveably coupled with a mateable mechanism 212 disposed on the proximal end of the distal shaft 206 as shown. More specifically, as best shown in FIG. 12B, in this exemplary implementation, the mateable mechanism 210 on the proximal shaft 204 is two elongate outer protrusions (or "ribs") 210A, 210B defining an inner channel 210C disposed therebetween. Further, as best shown in FIGS. 12B and 12C, the mateable mechanism 212 is an elongate protrusion 212 that is mateable with and slidable within the inner channel 210C as shown. Further, the elongate protrusion 212 has two wings 212A, 212B (as best shown in FIG. 12C) that extend from the protrusion 212 such that the wings 212A, 212B slidably fit within two transverse channels 211A, 211B that are defined within the inner channel 210C (as best shown in FIG. 12B). As such, the two wings 212A, 212B help to retain the protrusion 212 within the channel 210C. Alternatively, the mateable mechanisms 210, 212 can be any known structures, features, or mechanisms that can mateably and slidably coupled to allow for movement of the two shafts 204, 206 in relation to each other via the mateable mechanisms 210, 212.

Figures 11E, 11F, 11G:
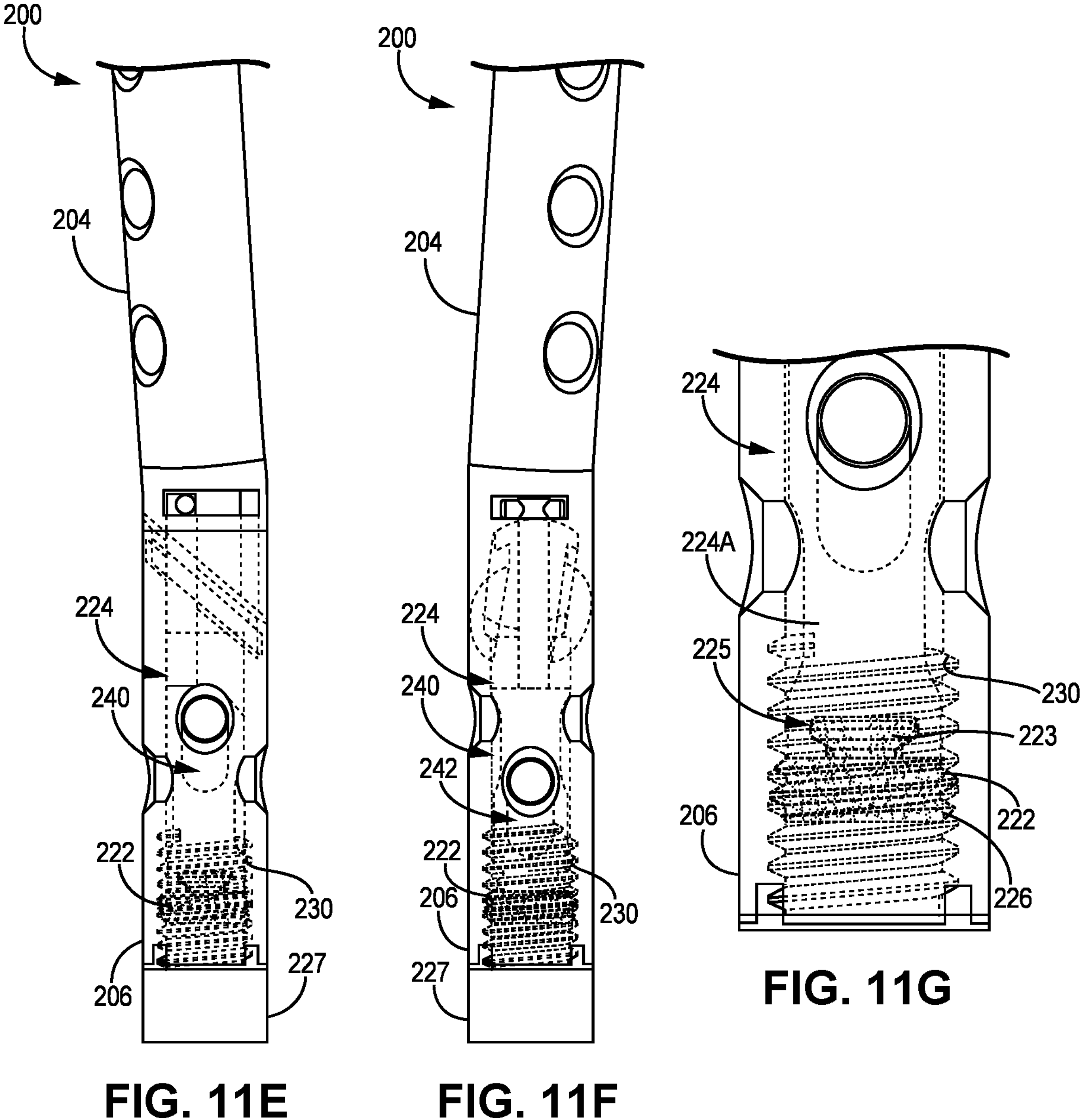
FIG. 11F is another expanded side view of the portion of the fixation device of FIG. 11E in the aligned position, according to one embodiment.
FIG. 11E is yet another expanded side view of more of the fixation device of FIG. 11A in the aligned position, according to one embodiment.
FIG. 11G is further expanded side view of the drive mechanism of the fixation device of FIG. 11A, according to one embodiment.

As shown in FIGS. 11A and 11C, the drive mechanism 220 disposed in the distal shaft 206 (and operably coupled to the proximal shaft 204) is made up of a rotatable drive screw 222 rotatably coupled to a linear driven shaft 224. More specifically, as best shown in FIGS. 11A-B, the drive screw 222 has external threads 226 defined thereon and is rotatably disposed within a lumen 228 defined within the distal shaft 206. Further, the drive screw 222 has a protrusion 223 that is rotatably disposed within a slot 225 defined within the driven shaft 224 (as best shown in FIG. 11G) such that the drive screw 222 can rotate freely in relation to the driven shaft 224. The lumen 228 has matching threads 230 (as also shown in FIG. 11G) defined on an inner surface near the distal end of the lumen 228 as shown.

As such, rotation of the drive screw 222 within the lumen 228 causes linear or axial movement of the driven shaft 224. As shown in FIGS. 11A-11D, the driven shaft 224 has slidable rods 230A, 230B at its proximal end that are slidably disposed within a radial slot 232 defined within the proximal shaft 204 such that the rods 230A, 230B can slide within the slot 232. In addition, as best shown in FIG. 11C, the drive screw 222 has a mateable connection component 234 defined or otherwise disposed at the distal end of the drive screw 222. The mateable connection component 234 can be any known mateable structure or mechanism 234 for receiving or coupling with a drive tool (not shown) such that the tool can be used to rotate the screw 222.

As shown in FIGS. 11A, 11C, 11E, and 11F, the distal end of the distal shaft 206 can also have a removable cap 227 removably attached thereto. More specifically, in certain embodiments, the cap 227 can have external threads 229 (as shown in FIGS. 11A and 11C) that can be inserted into the distal end of the lumen 228 through a distal opening 221 (as shown in FIGS. 11B and 11D) and threadably coupled to the internal threads 230 of the lumen 228. Further, the cap 227 can have a mateable structure or mechanism 231 that can be coupled to a tool to attach the cap 227 to the distal shaft 206 or remove the cap 227 therefrom. When the cap 227 is removed, the mateable connection component 234 of the drive screw 222 can be accessed by a tool (not shown) to rotate the screw 222 and thus actuate the drive mechanism 220 as will be described below.

In a further alternative, the internal threads 230 of the lumen 228 in this embodiment (and in any other implementation herein) can also be used for removal of the device 200. That is, if it is desirable to extract or otherwise remove the device 200 from the target bone, the cap 227 as discussed above can be removed (if the cap was previously attached) and a removal tool (not shown) with external threads on its outer surface can be inserted into the lumen 228 and threadably coupled to the threads 230 within the lumen 228. Once the removal tool is attached to the distal shaft 206 via the threads, the tool can then be used to remove the device 200 from the bone.

According to one embodiment, as best shown in FIGS. 11A-11D, the driven shaft 224 has a distal section 224A and a proximal section 224B extending from the distal section 224A. In one implementation as shown, the distal section 224A is slidably disposed within the lumen 228 such that the distal section 224A can move axially within the lumen 228. Further, the proximal section 224B has a smaller diameter than the distal section 224A and extends from the distal shaft 206 into the proximal shaft 204 across the joint 208 as shown.

In certain implementations as best shown in FIGS. 11E, 11F, and 12A, the drive shaft 224 can have two slots 240, 242 defined through the shaft 224. Each of the slots 240, 242 is defined within the shaft 224 such that they are in communication with corresponding lumens 244, 246 defined in the distal shaft 206 as best shown in FIGS. 12A and 12B. More specifically, the distal shaft 206 can have two lumens 244, 246 configured to receive fixation screws (or other known attachment mechanisms) 248, 250 as best shown in FIGS. 12A-12C. The slots 240, 242 are defined in the shaft 224 such that the slots 240, 242 allow for the fixation screws 248, 250 to be disposed through the distal shaft 206 and the axially slidable drive shaft 224 while allowing for the drive shaft 224 to freely move axially as necessary for operation of the drive mechanism 220 as discussed above. More specifically, the lumen 244 is in communication with the slot 240 such that the screw 248 can be positioned through the lumen 244 and slot 240 regardless of the axial position of the drive shaft 224 within the distal shaft 206. Similarly, the lumen 246 is in communication with the slot 242 such that the screw 250 can be positioned through the lumen 246 and slot 242 regardless of the axial position of the drive shaft 224 within the distal shaft 206. Thus, the drive mechanism 220 can be used to urge the device 200 between the insertion and articulated positions as discussed elsewhere herein while the screws 248, 250 are inserted through the distal shaft 206 (and the bone that the device 200 is positioned within).

According to some embodiments, the two lumens 244, 246 are defined through the distal shaft 206 (and the corresponding slots 240, 242 in the drive shaft 224) at different angles in relation to each other. In certain specific implementations, the axes of the two lumens 244, 246 (and corresponding slots 240, 242) are substantially transverse in relation to each other. Further, in certain embodiments, the lumens 244, 246 have threads defined within the inner surfaces of the lumens 244, 246 such that the screws 248, 250 can mateably couple to the distal shaft 206 via the threads on the external surface of the screws 248, 250 and the threads defined in the inner surfaces of the lumens 244, 246. Alternatively, the lumens 244, 246 do not have threads defined therein.

As shown in FIGS. 12A-12C, the proximal shaft 204 according to one embodiment has a proximal portion (or length) 204A and a distal portion 204B, wherein the distal portion 204B has a greater diameter than the proximal portion 204A. According to one embodiment, the distal portion 204B has a diameter ranging from about 0.5 mm to about 15, while the proximal portion 204A has a diameter ranging from about 2 mm to about 4 mm. Further, the distal portion 204B has three lumens 260A, 260B, 260C defined therein, each of which is configured to receive a fixation screw 262A, 262B, 262C as shown or other similar mechanism. The greater diameter of the distal portion 204B makes it possible to have the three lumens 260A, 260B, 260C, thereby providing greater stability and fixation in comparison to known devices without such a distal portion and three such openings.

Each of the three openings 260A-C have an axis that is substantially transverse to the longitudinal axis of the proximal shaft 204 (and the distal portion 204B). In one embodiment as shown, the axes of the three openings 260A-C are not parallel with each other. More specifically, as shown in FIGS. 12A-12C, each of the three openings 260A-C has an axis that is not parallel to either of the two openings 260A-C. In accordance with one exemplary embodiment, each axis has an angle that is offset by about 5 degrees in relation to the axes of the other two openings. Thus, opening 260B has an axis that is offset by about 5 degrees in relation to the opening 260A, and opening 260C has an axis that is offset by about 5 degrees in relation to opening 260B. In one specific exemplary implementation, the plane for each opening 260A-C is oriented at 15, 20, and 25 degrees respectively from the anterior/posterior plane.

In one embodiment, the center of opening 260A is disposed at about 59 mm from the distal end of the device 200, while the center of opening 260B is disposed at about 49.5 mm from the distal end of the device 200, and the center of opening 260C is disposed at about 40 mm from the distal end of the device 200. Alternatively, the location of each opening 260A-C can vary by about 1 mm to about 5 mm in either direction in relation to the exemplary locations set forth above.

Further, in certain embodiments, the lumens 260A-C have no threads defined within the inner surfaces of the lumens 260A-C. In such implementations, the screws 262A-C (or other similar mechanisms), which can be threaded as shown, do not attach to the proximal shaft 204 via threads or any other mechanism and instead are simply disposed through the lumens 260A-C and attach to the bone through which the screws 262-C are disposed on either side of the shaft 204. Alternatively, the lumens 260A-C have threads defined therein.

Figure 15A:
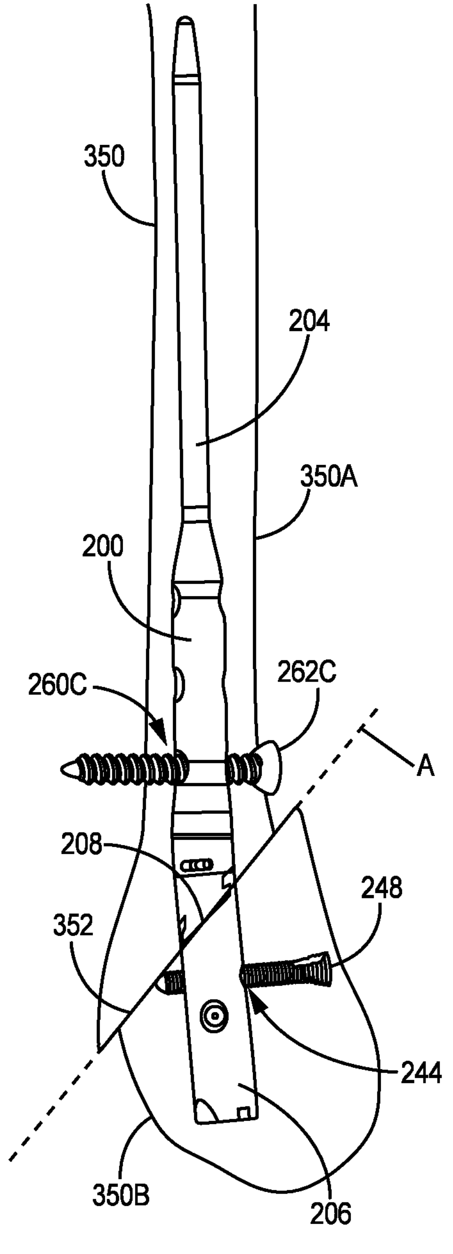
FIG. 15A is a side view of a fractured bone with a displaced fracture and a fixation device disposed within the fractured bone, according to one embodiment.

In use according to various implementations, the device 200 is placed within a fractured fibula or other target bone such that the joint 208 is substantially adjacent to the fracture. For example, in one exemplary embodiment as shown in FIG. 15A, the device 200 (or any other device embodiment disclosed or contemplated herein, such as device 10, 50, 100, or 300) can be inserted into the fractured target bone 350. Further, while positioning the device 200 within the bone 350 as desired, the device 200 can be rotated to ensure that the angle of the joint 208 is substantially parallel to the angle of the fracture 352 as represented by the line A in FIG. 15A. Once the device 200 is positioned as desired, at least one fixation screw (or other attachment device) (such as screw 262C, for example) can be inserted through the bone portion 350A above the fracture 352 and through a lumen (such as lumen 260C) in the proximal shaft 204. Further, at least one fixation screw (or other attachment device) (such as screw 248) can be inserted through the bone portion 350B below the fracture 352 and through a lumen (such as lumen 244) in the distal shaft 206.

Figure 15B:
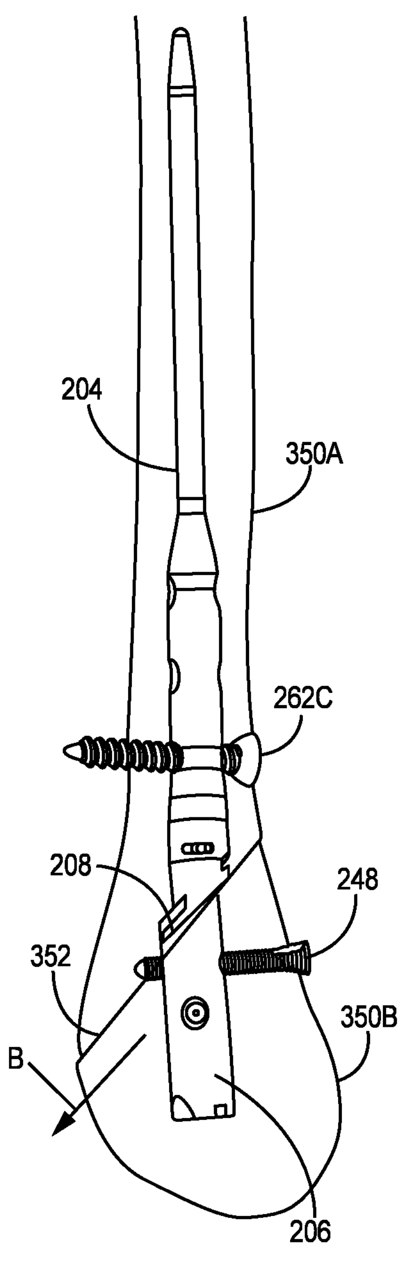
FIG. 15B is a side view of the fractured bone of FIG. 15A in which the fixation device has been actuated into its articulated position such that the device has reduced the fracture and realigned the bone, according to one embodiment.

As best shown in FIG. 15B, once each shaft 204, 206 of the device 200 is attached to one of the two fractured sections 350A, 350B of the bone 350, respectively, the drive mechanism (such as mechanism 220 as discussed in detail above) can be engaged to actuate the distal shaft 206 to move in relation to the proximal shaft 204 along the joint 208 such that the distal shaft 206 moves in a direction as shown via arrow B that is substantially parallel with the fracture 352 of the bone 350. And because the distal shaft 206 is attached to the bone section 350B via at least one fixation screw (such as screw 248), the distal shaft 206 thereby urges the bone section 350B to move in the same direction as indicated by arrow B in relation to the bone section 350A along the fracture 352. The drive mechanism can be actuated to urge the distal shaft 206 as shown until the bone section 350B has been urged back (or "realigned" or "articulated") into realignment with the bone section 350A, thereby reducing the fracture 352. Alternatively, the actuation of the drive mechanism can move both shafts 204, 206 in relation to each other and thereby reduce the fracture 352 and realign the bone 350. In a further alternative, the actuation of the drive mechanism can move the proximal shaft 204 in relation to the distal shaft 206 and thereby realign the bone 350.

According to one specific embodiment, the exemplary drive mechanism 220 as discussed above can be actuated to accomplish the bone realignment and fracture reduction in the following fashion. A drive tool (not shown) is inserted into the distal opening 221 of the distal shaft 206, into the lumen 228 and coupled with the drive screw 222 at the connection component 234. Once the drive tool is coupled to the drive screw 222, the tool can be used to rotate the drive screw 222, thereby causing the driven shaft 220 to move axially in one direction or the other, which causes the distal shaft 206 to move radially in one direction or the other in relation to the proximal shaft 204. For example, the device 200 can initially be disposed in the insertion configuration as shown in FIGS. 11A, 11B, 12C, and 15A. The drive tool can then be used to rotate the drive screw 222 such that the driven shaft 224 moves axially in the proximal direction. This causes the wings 230A, 230B to move in the proximal direction, which, as shown in FIGS. 11C, 11D, 12A, 12B, and 15B, urges distal shaft 206 to move distally and radially along the joint 208 via the slidable protrusion 212 as discussed above. And as the distal shaft 206 moves radially (to the "right" as shown in FIG. 11B, and to the "left" as shown in FIG. 15B), the rods 230A, 230B move only axially such that the position of the rods 230A, 230B change within the slot 232 as shown. Alternatively, any drive mechanism according to any of the implementations disclosed or contemplated herein can be used to accomplish the fracture reduction and bone realignment as discussed herein.

Another device 300 implementation is depicted in FIGS. 13A-13D in which the device 300 has different outer diameters in comparison to the previous embodiments as shown in FIGS. 10A-B and 12A-C. Except as expressly discussed herein, the various components and features of this device 300 embodiment are substantially similar or identical to the components and features of the various embodiments disclosed or contemplated above and depicted in FIGS. 2-12C. In this implementation, the device 300 has a device body 302 with a proximal elongate section 304 and a distal elongate section 306 that are adjustably coupled to each other at the joint 308 such that the drive mechanism 310 can cause the two sections 304, 306 to move substantially radially (and, in some cases, axially as well) in relation to each other. However, unlike the previous embodiments as discussed above, the device 300 has three different diameters along its length. More specifically, the proximal shaft 304 has a proximal portion (or length) 304A, a middle portion (or length) 304B, a distal portion (or length) 304C, along with a proximal transition portion (or length) 304D between the proximal and middle portions 304A, 304B, and a distal transition portion (or length) 304E between the middle and the distal portions 304B, 304C, wherein the distal portion 304C has a greater diameter than the middle portion 304B and the middle portion 304B has a greater diameter than the proximal portion 304A. Further, the distal shaft 306 has the same diameter as the distal portion 304B of the proximal shaft 304. In addition, the device 300 also has a tip 312 at the proximal end of the proximal shaft 304 that has a narrowing diameter along the length of the tip 312 from the distal end to the proximal end of the tip 312 as shown.

According to one exemplary embodiment, the distal shaft 306 and the distal portion 304C of the proximal shaft 304 have a diameter of 7 mm, while the middle portion 304B of the proximal shaft 304 has a diameter of about 6 mm and the proximal portion 304A has a diameter of about 3 mm. Alternatively, the distal shaft 306 and distal portion 304C of the proximal shaft 304 can have a diameter ranging from about 1 mm to about 6 mm, the middle portion 304B can have a diameter ranging from about 3 mm to about 12 mm, and the proximal portion 304A can have a diameter ranging from about 4 mm to about 12 mm.

In some implementations, the proximal tip 312 has a length of about 7 mm, the proximal portion 304A of the proximal shaft 304 has a length of about 49 mm, the proximal transition portion 304D has a length of about 8.5 mm, the middle portion 304B and the distal transition portion 304E have a combined length of about 26.5 mm, and the distal portion 304C and the distal shaft 306 have a combined length of about 34 mm. Alternatively, the proximal tip 312 can have a length ranging from about 1 mm to about 20 mm, the proximal portion 304A can have a length ranging from about 10 mm to about 500 mm, the proximal transition portion 304D has a length ranging from about 5 mm to about 30 mm, the middle portion 304B and the distal transition portion 304E can have a combined length ranging from about 10 mm to about 500 mm, and the distal portion 304C and the distal shaft 306 can have a combined length ranging from about 10 mm to about 500 mm.

Further, the middle portion 304B of the proximal shaft 304 has three lumens 314A, 314B, 3140 defined therein, each of which is configured to receive a fixation screw (not shown) or other similar mechanism. The lumen 314A-C can be substantially similar to the lumens 160A-C and/or the lumens 260A-C in the embodiments discussed above, including the dimensions and features thereof.

Figure 14:
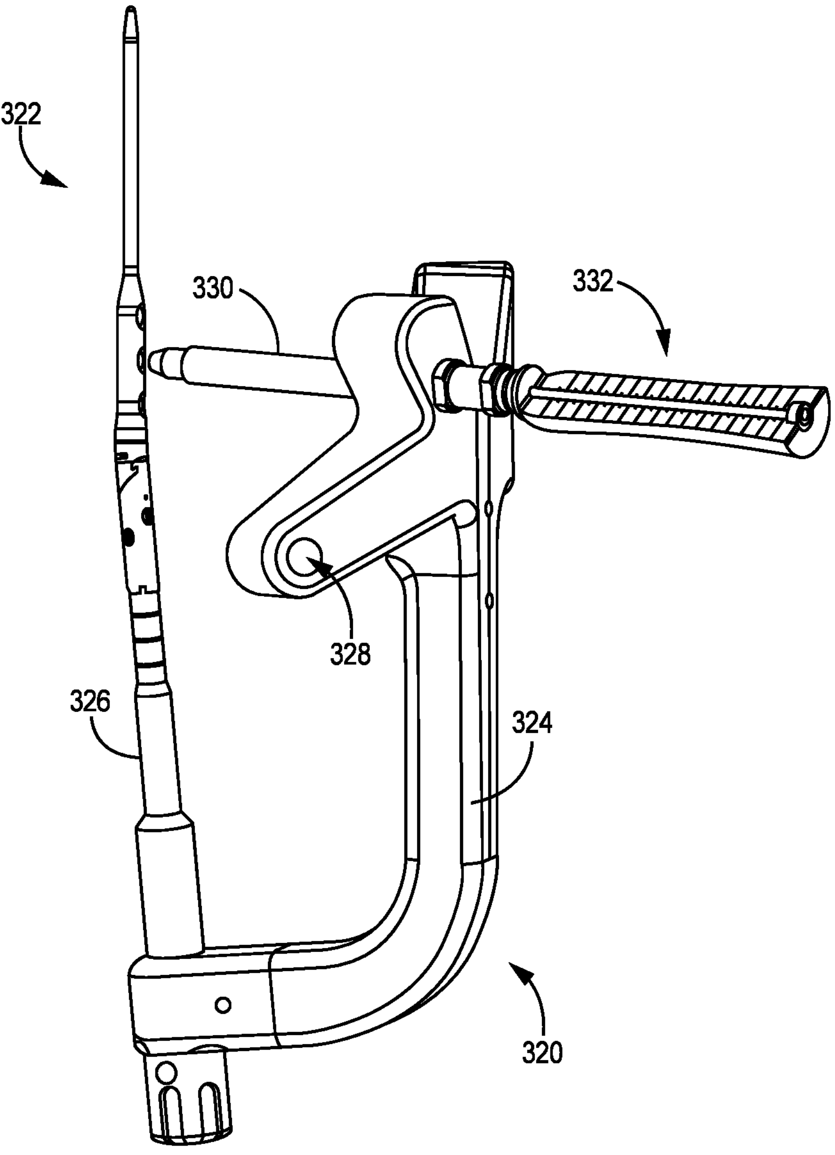
FIG. 14 is a perspective view of a positioning device, according to one embodiment.

FIG. 14 depicts one example of a positioning device 320 that can be used to position any of the bone fixation device embodiments disclosed or contemplated herein. More specifically, the positioning device 320 according to certain embodiments can assist with both inserting and positioning the bone fixation device and further can serve as a drill guide for correct positioning of fixation screws. For example, as shown in the figure, the positioning device 320 is used to position an exemplary bone fixation device 322 while also providing a drill guide 330 for positioning the fixation screws that will fix the device 322 in place within the target bone. The positioning device 320 has a device body 324 with a fixation device attachment structure 326 at a proximal end of the device 320 and at least two openings (such as opening 328) through which a drill guide 330 can be positioned at the distal end of the device 320, with depth gauge 332 provided thereon for determining the appropriate fixation screw length. In use, the bone fixation device 322 is attached to the attachment structure 3326 as shown, and then the bone fixation device 322 is urged into the target bone (not shown) using the positioning device 320. Once the fixation device 322 is positioned within the target bone as desired, a drill guide (such as the guide 330 as shown) can be inserted into the appropriate one of the drill guide openings 328 to ensure that the drill and the fixation screw are positioned correctly to ensure that the fixation screw is positioned through a fixation screw lumen in the bone fixation device 322 (as described elsewhere herein). Once the fixation screws are inserted as desired, the positioning device 320 can be removed.

While the various systems described above are separate implementations, any of the individual components, mechanisms, or devices, and related features and functionality, within the various system embodiments described in detail above can be incorporated into any of the other system embodiments herein.

The terms "about" and "substantially," as used herein, refers to variation that can occur (including in numerical quantity or structure), for example, through typical measuring techniques and equipment, with respect to any quantifiable variable, including, but not limited to, mass, volume, time, distance, wave length, frequency, voltage, current, and electromagnetic field. Further, there is certain inadvertent error and variation in the real world that is likely through differences in the manufacture, source, or precision of the components used to make the various components or carry out the methods and the like. The terms "about" and "substantially" also encompass these variations. The term "about" and "substantially" can include any variation of 5% or 10%, or any amount—including any integer—between 0% and 10%. Further, whether or not modified by the term "about" or "substantially," the claims include equivalents to the quantities or amounts.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range. Although the various embodiments have been described with reference to preferred implementations, persons skilled in the art will recognize that changes may be made in form and detail without departing from the spirit and scope thereof.

Although the various embodiments have been described with reference to preferred implementations, persons skilled in the art will recognize that changes may be made in form and detail without departing from the spirit and scope thereof.

What is claimed is:

1. A bone fixation device comprising:

(a) a device body comprising:

(i) a proximal member comprising:

(A) a shaft lumen defined within the proximal member, wherein the shaft lumen is parallel to a longitudinal axis of the proximal member; and (B) a drive slot defined with the proximal member, wherein the drive slot is transverse to the longitudinal axis of the proximal member;

(ii) a distal member comprising:

(A) a drive mechanism lumen defined within the distal member, wherein the drive mechanism lumen is parallel to a longitudinal axis of the distal member; and (B) at least one fixation lumen defined within the distal member, wherein the at least one fixation lumen is transverse to the longitudinal axis of the distal member, wherein the at least one fixation lumen is in fluidic communication with the drive mechanism lumen;

(b) an adjustable joint formed between the proximal member and the distal member, wherein the proximal member and the distal member are movable radially and axially in relation to each other via the adjustable joint; and (c) a drive mechanism operably coupled to the proximal and distal members, the drive mechanism comprising:

(i) a rotatable drive structure rotatably disposed within the drive mechanism lumen, wherein the rotatable drive structure comprises a rotatable engagement structure disposed at a proximal end of the rotatable drive structure; and (ii) a linear drive shaft slidably disposed within the drive mechanism lumen, the linear drive shaft comprising:

(A) a stationary engagement structure disposed at a distal end of the linear drive shaft, wherein the stationary engagement structure is configured to couple with the rotatable engagement structure;

(B) at least one transverse lumen defined through the linear drive shaft, wherein the at least one transverse lumen is transverse to a longitudinal axis of the linear drive shaft, wherein the at least one transverse lumen is in fluidic communication with the at least one fixation lumen, wherein the at least one transverse lumen comprises first and second transverse lumens, wherein the first transverse lumen has a longitudinal axis that is transverse to a longitudinal axis of the second transverse lumen; and (C) at least one protrusion disposed at a proximal end of the linear drive shaft, wherein the at least one protrusion is slidably disposed within the drive slot.

2. The device of claim 1, wherein rotation of the rotatable drive structure within the drive mechanism lumen causes the linear drive shaft to move axially within the drive mechanism lumen.

3. The device of claim 1, wherein the rotatable drive structure is threadably coupled to an inner surface of the drive mechanism lumen.

4. The device of claim 1, wherein the at least one fixation lumen comprises first and second fixation lumens, wherein the first fixation lumen has a longitudinal axis that is transverse to a longitudinal axis of the second fixation lumen.

5. The device of claim 1, wherein the at least one fixation lumen comprises threads defined in an inner wall of the at least one fixation lumen.

6. The device of claim 1, wherein the adjustable joint comprises:

(a) a distal face disposed at an angle ranging from 1 degree to 89 degrees in relation to the longitudinal axis of the proximal member; and (b) a proximal face disposed at an angle corresponding to the angle of the distal face such that the proximal member is in slidable contact with the distal member.

7. The device of claim 1, wherein the linear drive shaft comprises a proximal section comprising a proximal section diameter and a distal section comprising a distal section diameter, wherein the distal section diameter is greater than the proximal section diameter.

8. The device of claim 1, wherein the at least one fixation lumen comprises threads defined in an inner wall of the at least one fixation lumen.

9. A bone fixation device comprising:

(a) a device body comprising:

(i) a proximal member comprising:

(A) a shaft lumen defined within the proximal member, wherein the shaft lumen is parallel to a longitudinal axis of the proximal member; and (B) a drive slot defined with the proximal member, wherein the drive slot is transverse to the longitudinal axis of the proximal member;

(ii) a distal member comprising:

(C) a drive mechanism lumen defined within the distal member, wherein the drive mechanism lumen is parallel to a longitudinal axis of the distal member; and (D) at least one fixation lumen defined within the distal member, wherein the at least one fixation lumen is transverse to the longitudinal axis of the distal member, wherein the at least one fixation lumen is in fluidic communication with the drive mechanism lumen;

(b) an adjustable joint formed between the proximal member and the distal member, wherein the proximal member and the distal member are movable radially and axially in relation to each other via the adjustable joint; and (c) a drive mechanism operably coupled to the proximal and distal members, the drive mechanism comprising:

(i) a rotatable drive structure rotatably disposed within the drive mechanism lumen, wherein the rotatable drive structure comprises a rotatable engagement structure disposed at a proximal end of the rotatable drive structure; and (ii) a linear drive shaft slidably disposed within the drive mechanism lumen, the linear drive shaft comprising:

(A) a proximal section comprising a proximal section diameter and a distal section comprising a distal section diameter, wherein the distal section diameter is greater than the proximal section diameter;

(B) a stationary engagement structure disposed at a distal end of the linear drive shaft, wherein the stationary engagement structure is configured to couple with the rotatable engagement structure;

(C) at least one transverse lumen defined through the linear drive shaft, wherein the at least one transverse lumen is transverse to a longitudinal axis of the linear drive shaft, wherein the at least one transverse lumen is in fluidic communication with the at least one fixation lumen, wherein the at least one transverse lumen is defined in the distal section; and (D) at least one protrusion disposed at a proximal end of the linear drive shaft, wherein the at least one protrusion is slidably disposed within the drive slot.

10. The device of claim 9, wherein rotation of the rotatable drive structure causes the linear drive shaft to move axially within the drive mechanism lumen.

11. The device of claim 9, wherein the rotatable drive structure is threadably coupled to an inner surface of the drive mechanism lumen.

12. The device of claim 9, wherein the at least one fixation lumen comprises first and second fixation lumens, wherein the first fixation lumen has a longitudinal axis that is transverse to a longitudinal axis of the second fixation lumen.

13. A bone fixation device comprising:

(a) a device body comprising:

(i) a proximal member comprising:

(A) a shaft lumen defined within the proximal member, wherein the shaft lumen is parallel to a longitudinal axis of the proximal member; and (B) a drive slot defined with the proximal member, wherein the drive slot is transverse to the longitudinal axis of the proximal member;

(ii) a distal member comprising:

(E) a drive mechanism lumen defined within the distal member, wherein the drive mechanism lumen is parallel to a longitudinal axis of the distal member; and (F) at least one fixation lumen defined within the distal member, wherein the at least one fixation lumen is transverse to the longitudinal axis of the distal member, wherein the at least one fixation lumen is in fluidic communication with the drive mechanism lumen;

(b) an adjustable joint formed between the proximal member and the distal member, wherein the proximal member and the distal member are movable radially and axially in relation to each other via the adjustable joint;

(c) a drive mechanism operably coupled to the proximal and distal members, the drive mechanism comprising:

(i) a rotatable drive structure rotatably disposed within the drive mechanism lumen, wherein the rotatable drive structure comprises a rotatable engagement structure disposed at a proximal end of the rotatable drive structure; and (ii) a linear drive shaft slidably disposed within the drive mechanism lumen, the linear drive shaft comprising:

(A) a stationary engagement structure disposed at a distal end of the linear drive shaft, wherein the stationary engagement structure is configured to couple with the rotatable engagement structure;

(B) at least one transverse lumen defined through the linear drive shaft, wherein the at least one transverse lumen is transverse to a longitudinal axis of the linear drive shaft, wherein the at least one transverse lumen is in fluidic communication with the at least one fixation lumen; and (C) at least one protrusion disposed at a proximal end of the linear drive shaft, wherein the at least one protrusion is slidably disposed within the drive slot; and (d) a removable cap, wherein the removable cap is removably coupleable to a distal opening defined in the distal member, wherein the distal opening is in fluidic communication with the drive mechanism lumen.

14. A bone fixation device comprising:

(a) a device body comprising:

(i) a proximal member comprising:

(A) a proximal lumen defined within the proximal member, wherein the proximal lumen is parallel to a longitudinal axis of the proximal member; and (B) a drive slot defined with the proximal member and in fluidic communication with the proximal lumen, wherein the drive slot is transverse to the longitudinal axis of the proximal member;

(ii) a distal member comprising:

(A) a distal lumen defined within the distal member, wherein the distal lumen is parallel to a longitudinal axis of the distal member, wherein the distal lumen is in fluidic communication with the proximal lumen; and (B) at least one fixation lumen defined within the distal member, wherein the at least one fixation lumen is transverse to the longitudinal axis of the distal member, wherein the at least one fixation lumen is in fluidic communication with the distal lumen;

(b) a slidable joint formed between the proximal member and the distal member, wherein the distal member is movable radially and axially in relation to the proximal member via the slidable joint; and (c) a drive mechanism operably coupled to the proximal and distal members, the drive mechanism comprising:

(i) a rotatable drive structure rotatably disposed within the distal lumen, wherein the rotatable drive structure comprises a first engagement structure disposed at a proximal end of the rotatable drive structure, wherein the first engagement structure comprises a substantially round protrusion extending proximally from the rotatable drive structure; and (ii) a linear drive shaft slidably disposed within the proximal lumen and the distal lumen, the linear drive shaft comprising:

(A) a second engagement structure disposed at a distal end of the linear drive shaft, wherein the second engagement structure is operably coupled with the first engagement structure, wherein the second engagement structure comprises an engagement slot sized and shaped to receive the first engagement structure such that the first engagement structure is rotatable in relation to the linear drive shaft but is not moveable axially in relation to the linear drive shaft;

(B) at least one transverse lumen defined through the linear drive shaft, wherein the at least one transverse lumen is transverse to a longitudinal axis of the linear drive shaft, wherein the at least one transverse lumen is in fluidic communication with the at least one fixation lumen; and (C) at least one radial protrusion disposed at a proximal end of the linear drive shaft, wherein the at least one radial protrusion is slidably disposed within the drive slot.

15. The device of claim 14, wherein the distal member is movable radially and axially in relation to the proximal member via the slidable joint between an aligned position in which the longitudinal axis of the distal member is substantially coaxial with the longitudinal axis of the proximal member and an articulate position in which the longitudinal axis of the distal member is non-coaxial and parallel with the longitudinal axis of the proximal member.

16. The device of claim 14, wherein rotation of the rotatable drive structure within the drive mechanism lumen causes the linear drive shaft to move axially within the distal lumen.

17. The device of claim 14, wherein the rotatable drive structure is threadably coupled to an inner surface of the distal lumen.

18. The device of claim 14, wherein the at least one fixation lumen comprises first and second fixation lumens, wherein the first fixation lumen has a longitudinal axis that is transverse to a longitudinal axis of the second fixation lumen.

19. The device of claim 14, wherein the at least one fixation lumen comprises threads defined in an inner wall of the at least one fixation lumen.

20. The device of claim 14, wherein the linear drive shaft comprises a proximal section comprising a proximal section diameter and a distal section comprising a distal section diameter, wherein the distal section diameter is greater than the proximal section diameter.

* * * * *